US012788619B2

(12) United States Patent
Mccallum et al.

(10) Patent No.: US 12,788,619 B2
(45) Date of Patent: Nov. 10, 2026

(54) UNIVERSAL METHOD FOR CREATING A CUSTOMIZED OBSTRUCTIVE SLEEP APNEA PREVENTION APPLIANCE

(71) Applicant: Anemed, Inc., Cleveland, OH (US)

(72) Inventors: Grant Mccallum, Cleveland, OH (US); Dominique Durand, Cleveland, OH (US)

(73) Assignee: Anemed, Inc., Cleveland, OH (US)

( * ) Notice: Subject to any disclaimer, the term of this patent is extended or adjusted under 35 U.S.C. 154(b) by 0 days.

(21) Appl. No.: 19/475,179

(22) PCT Filed: Apr. 15, 2024

(86) PCT No.: PCT/US2024/024599

§ 371 (c)(1),
(2) Date: Oct. 14, 2025

(87) PCT Pub. No.: WO2024/216254

PCT Pub. Date: Oct. 17, 2024

(65) Prior Publication Data

US 2026/0232482 A1 Aug. 13, 2026

Related U.S. Application Data

(60) Provisional application No. 63/551,546, filed on Feb. 9, 2024, provisional application No. 63/496,124, filed on Apr. 14, 2023.

(51) Int. Cl.
*A61F 5/56* (2006.01)
*B33Y 50/00* (2015.01)
(Continued)

(52) U.S. Cl.
CPC .............. *A61F 5/566* (2013.01); *B33Y 50/00* (2014.12); *B33Y 80/00* (2014.12); *G06T 7/0012* (2013.01);
(Continued)

(58) Field of Classification Search
CPC ...... A61F 5/566; A61F 2005/563; A61C 7/36; A61C 7/002; A61C 7/08; A61C 7/00;
(Continued)

(56) References Cited

U.S. PATENT DOCUMENTS

2014/0315153 A1* 10/2014 Kitching ............ B29C 33/3842 433/213
2019/0105842 A1* 4/2019 Dau ....................... B33Y 50/00
(Continued)

OTHER PUBLICATIONS

PCT Search Report and Written Opinion for corresponding Application Serial No. PCT/US2024/024599 with a date of mailing Aug. 22, 2024, 13 pages.

*Primary Examiner* — Rachael E Bredefeld
*Assistant Examiner* — Kevin S Albers
(74) *Attorney, Agent, or Firm* — Tarolli, Sundheim, Covell & Tummino LLP

(57) ABSTRACT

An obstructive sleep apnea (OSA) prevention appliance can be made according to a common path but customized for a user using at least a 3D oral scan taken with a first imaging modality and a 3D reconstruction formed with a plurality of images taken with a second imaging modality different from the first imaging modality. The 3D oral scan and the 3D reconstruction can be aligned and registered together for use in creating a customized model of the OSA prevention appliance. The model can be created by orienting and positioning two model cylinders with respect to aspects of the user's mouth anatomy, forming a model of a mouthguard based on the model cylinders and the anatomy, and modeling a wire configured to hold at least a portion of the tongue from collapsing during sleep. The model can be used to produce the OSA prevention appliance for the user.

19 Claims, 26 Drawing Sheets

(51) Int. Cl.
*B33Y 80/00* (2015.01)
*G06T 7/00* (2017.01)
*G06T 17/00* (2006.01)

(52) U.S. Cl.
CPC .... *G06T 17/00* (2013.01); *G06T 2207/30036* (2013.01)

(58) Field of Classification Search
CPC ..... A61C 13/0004; A61C 13/20; A61C 13/34; A61C 9/004; A61C 9/0053; A61C 9/00; A61C 9/0046; A61C 19/066; B33Y 50/00; B33Y 80/00; G06T 7/0012; G06T 7/00; G06T 7/11; G06T 7/12; G06T 7/33; G06T 2207/30036; G06T 2207/10024; G06T 2207/10081; G06T 2210/41; G06T 11/00; G06T 15/04; G06T 19/00
USPC .......................................................... 128/848
See application file for complete search history.

(56) References Cited

U.S. PATENT DOCUMENTS

| | | | | |
|---|---|---|---|---|
| 2020/0060866 | A1* | 2/2020 | Durand | A61F 5/566 |
| 2022/0280333 | A1* | 9/2022 | Wang | A61F 5/566 |
| 2025/0213335 | A1* | 7/2025 | Lee | A61C 7/002 |

* cited by examiner

300

400

500

600

702

704

802

804

806

902

904

1102

1104

1502

1504

1602

1604

1702

1704

1706

1802

1804

1902

1904

2302

2304

UNIVERSAL METHOD FOR CREATING A CUSTOMIZED OBSTRUCTIVE SLEEP APNEA PREVENTION APPLIANCE

CROSS REFERENCE TO RELATED APPLICATIONS

This application claims the benefit of U.S. Provisional Application Ser. No. 63/496,124, filed 14 Apr. 2023, entitled "METHOD FOR PRODUCING AN OROPHARYNX PROTECTION APPLIANCE". This application also claims the benefit of U.S. Provisional Application Ser. No. 63/551,546, filed 9 Feb. 2024, entitled "METHOD FOR PRODUCING AN OROPHARYNX PROTECTION APPLIANCE". The entireties of these applications are incorporated by reference for all purposes.

TECHNICAL FIELD

This disclosure relates generally to obstructive sleep apnea (OSA) prevention and more specifically to a universal and improved method for customizing an OSA prevention appliance for any given user.

BACKGROUND

Obstructive sleep apnea (OSA) affects at least 39 million patients in the US alone and is characterized by the recurrent collapse of soft tissue occluding the upper airway during sleep. The airway obstruction leads to pauses in breathing or instances of shallow or infrequent breathing that can happen many times during the night. Individuals with such an airway obstruction are rarely aware of their difficulty breathing, even upon awakening, causing poor diagnosis and treatment rates. No pharmaceutical based therapies exist to treat sleep apnea. Although several mechanical therapies exist, such as continuous positive airway pressure (CPAP) therapy or mandibular advancement device (MAD) treatment, these therapies are often improperly used, poorly tolerated, and/or ineffective, causing users to stop using the therapy. There remains a need for therapy that is a cost-effective, minimally invasive, and customized; however, new therapies are expensive, require significant FDA trials, and/or are not sufficiently customized for a given patient. A new OSA prevention appliance that is less invasive and more tolerated by users has been developed. The OSA prevention appliance requires customization for each patient and current methods are expensive, labor intensive, and take a significant amount of time for manufacture of each single OSA prevention appliance.

SUMMARY

Described herein is a universal method (executed by a system comprising a processor) that can be followed by taking unique inputs (e.g., measurements, images, or the like) from any given user suffering from obstructive sleep apnea (OSA) to create customized OSA prevention appliances. The unique inputs can be user-specific images taken by different imaging modalities. For example, one imaging modality can be used to take a three dimensional oral scan of a portion of user's oral cavity (e.g., can include lower teeth, gums, and/or a portion of the mandible), while another imaging modality can take a plurality of two dimensional images that can be used to create a three dimensional reconstruction of another portion of the user's oral cavity (e.g., can include one or more lower teeth, at least the portion of the mandible, gums, tongue, cheek, etc., but can also include more features of the mouth) and a portion of the user's oropharynx.

At least two anatomical features can be identified in the oral scan and in the reconstruction. The at least two anatomical features can be aligned between the oral scan and the reconstruction, and the oral scan and the reconstruction can be registered together. A customized three-dimensional model of the user's anatomy can be created using the combined oral scan and reconstruction. Creating the customized three-dimensional model can include forming, positioning, and orienting models of two cylinders within the customized three-dimensional model of the user's anatomy in an axial plane relative to at least one tooth and/or the mandible of the user. A model of the OSA prevention appliance for the specific anatomy of the user can be formed utilizing the customized three-dimensional model of the user's anatomy and the model of the two cylinders for minimal invasiveness and good toleration by the user.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
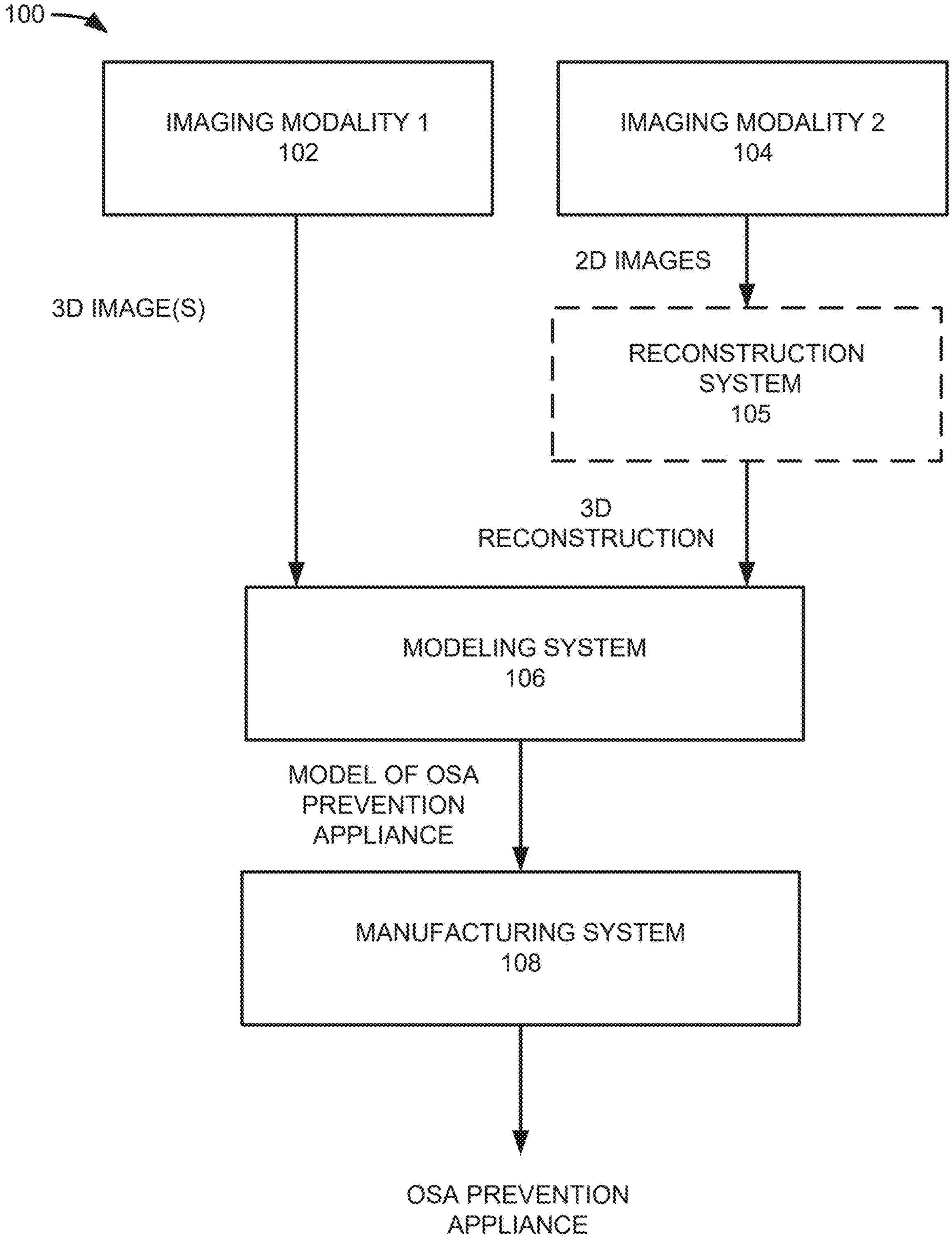
FIG. 1 is a block diagram showing a system that can customize an obstructive sleep apnea (OSA) prevention appliance according to a universal and improved method.

Unless otherwise defined, all technical terms used herein have the same meaning as commonly understood by one of ordinary skill in the art to which the present disclosure pertains.

As used herein, the singular forms "a," "an," and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As used herein, the term "obstructive sleep apnea", also referred to as "OSA", can refer to a sleep disorder that is caused by complete or partial obstruction of a subject's airway, leading to repetitive episodes of shallow or paused breathing during sleep, despite the subject's effort to breathe. In some instances, the obstruction can be due to a collapse of soft tissue (including at least a portion of the tongue) into the oropharynx of the upper airway.

As used herein, the term "oral cavity" can refer to what is colloquially known as the mouth and is the first portion of the digestive system. The oral cavity can be bounded by the lips, upper and lower jawbones, and the cheeks. The oral cavity can include at least the lips, the anterior oral portion of the tongue, the palates, teeth, gums, the uvula, the lining of the cheeks, at least a portion of the maxilla and the mandible, and the like.

As used herein, the term "mandible" can refer to the lower jawbone. The mandible is the most moveable bone in the skull and hosts the lower teeth. At least a portion of the mandible provides a lower bound of the oral cavity.

As used herein, the term "maxilla" can refer to the upper jawbone formed from the fusion of two maxillary bones. The maxilla can include at least the hard palate in the front of the mouth and can host the upper teeth. At least a portion of the mandible provides an upper bound of the oral cavity.

As used herein, the term "oropharynx" can refer to a part of the throat behind the mouth. The oropharynx and the oral cavity can include at least some of the same structures. The oropharynx can include at least the soft palate, the side and back walls of the throat, the tonsils, and at least a portion of the posterior pharyngeal part of the tongue.

As used herein, the term "appliance" can refer to a device designed to perform a specific task. The term "apparatus" may be used interchangeably with the term "appliance".

As used herein, the term "airway patency" can refer to the ability of a subject's airway to remain open and allow for adequate airflow; otherwise known as the ability to breath. Assessment of airway patency can include, but is not limited to, evaluating if there is an obstruction in the airway.

As used herein, the term "imaging modality" can refer to a technique and/or device that utilizes a given physical mechanism to generate an image of and/or that can detect internal anatomical structures (e.g., bone, muscle, fat, organs, blood, etc.) and/or physiological events.

As used herein, the term "oral scan" can refer to three-dimensional measurements of at least a patient's teeth and/or gums. The three-dimensional measurements are then used to create a detailed, digital, three-dimensional image of at least the patient's teeth and/or gums. The oral scan can be accomplished by an intraoral scanner that uses optical or laser technology to project a light onto the teeth and/or gums. The three-dimensional oral scan can be taken by an imaging modality using a handheld device configured to enter the patient's mouth.

As used herein, the term "cone beam computed tomography", also referred to as "CBCT", can refer to an imaging modality used by dental professionals, which is a variation of traditional computed tomography. A CBCT system rotates around a subject to capture data using a cone shaped x-ray beam, the data can include a plurality of 2D images at points during the rotation. The data is used to reconstruct a three-dimensional tomographic image of the subject's anatomy; for example the anatomy can include dental features (e.g., one or more teeth), the oral and maxillofacial region (e.g., including the mouth, jaw, and neck), and ears, nose, and throat (also referred to as ENT).

As used herein, the term "reconstruction" can refer to a mathematical process that generates three-dimensional tomographic images from x-ray projection data acquired at many different angles around the subject.

As used herein, the term "stereolithography", also referred to as "STL" that also refers to an associated file type, can refer to a three dimensional (also referred to as "3D") printing technology where each file is made up of a series of linked triangles that describe the surface geometry of a 3D model or object. STL may also be referred to as "standard triangle language" and/or "standard tessellation language".

As used herein, the terms "user", "patient", and "subject" can be used interchangeably and can refer to any warm-blooded organism, including, but not limited to, a human being, a pig, a rat, a mouse, a dog, a cat, a goat, a sheep, a horse, a monkey, an ape, a rabbit, a cow, etc.

II. Overview

Patients suffering from obstructive sleep apnea (OSA) experience a recurrent collapse of soft tissue occluding the upper airway during sleep, which leads to pauses in breathing or instances of shallow or infrequent breathing that can happen many times during the night. OSA has poor diagnosis rates at least in part because individuals are rarely aware of their difficulty breathing, even upon awakening, complicating the already poor diagnosis rates. Even when patients are diagnosed, there are no pharmaceutical based therapies available and mechanical therapies, such as continuous positive airway pressure (CPAP) therapy and mandibular advancement device (MAD) treatment, are often improperly used, poorly tolerated, and/or ineffective. Surgical therapies are also an option, but generally only used in the most severe cases due to the highly invasive nature.

A different type of mechanical device for prevention of OSA, the OSA prevention appliance (also referred to as oropharynx appliance to maintain airway patency, described in U.S. application Ser. No. 16/488,945, which is incorporated herein by reference in its entirety) has shown promise in treating and/or preventing OSA. This type of mechanical device (shown in, e.g., FIG. 13 of U.S. application Ser. No. 16/488,945) uses a passive tongue retention structure (e.g., a wire) held by an anchoring structure anchored to a mouthguard and is cheaper, less invasive, and easier to use that other solutions. Each OSA prevention appliance is manufactured specifically for each respective patient, making each device customized for high user tolerance and minimized negative side effects, but the process used to customize each OSA prevention appliance is prohibitively long and labor intensive.

Described herein is a universal method for manufacturing OSA prevention appliances that are customized for any given user. The method can provide a common path for all customization to follow vastly improving the amount of time and labor it takes to customize an OSA prevention appliance. In other words, the method involves extracting and processing information from multiple imaging modalities to create a custom, tightly fitted OSA prevention appliance for each patient. For example, a three-dimensional oral scan can include a three-dimensional image of the patient's teeth and gums, which can be formed from images taken with an intraoral scanner, and a three-dimensional reconstruction can be created based on curved beam computed tomography (CBCT) images that shows the anatomical position of the soft tissue of the tongue/oropharynx/airway boundary relative to a location of the patient's teeth. From the specific anatomy of each patient (e.g., shown in images), the universal method can form a customized OSA prevention appliance for each patient.

III. Systems

Described herein is a system 100 that can customize an obstructive sleep apnea (OSA) prevention appliance according to a universal and improved method. It should be understood that different algorithms can be used to guide the method that receives images of at least a portion of a user's mouth (at least one being a three-dimensional image) as input and outputs a fully customized OSA prevention appliance. Previously, the concept of an OSA prevention appliance to at least partially prevent, treat, and/or alleviate sleep apneas in patients with OSA was described (e.g., an oropharynx appliance to maintain airway patency (non-exclusive example shown in FIG. 13 of U.S. application Ser. No. 16/488,945)). This example of the OSA prevention appliance can include a mouthguard removably attached over the lower teeth and a wire, attached to the mouthguard, that holds the tongue to prevent collapse into the oropharynx. Advantageously, this OSA prevention appliance can prevent movement (e.g., collapse) of the tongue into the oropharynx during sleep and, therefore, is ideal for patients with obstructive sleep apnea and/or excessive snoring (which is often thought of as a precursor to and/or a symptom of obstructive sleep apnea). In use, the OSA prevention appliance can be placed in the subject's mouth at night like a regular mouth guard and the wire can hold back the tongue from blocking the oropharynx. The OSA prevention appliance can be fitted to the subject's mouth so that the mouthguard fits tightly onto the lower teeth and the wire is at a precise position to stop the tongue from blocking the oropharynx while allowing swallowing and not causing a feeling of choking.

Notably, the OSA prevention appliance can at least partially prevent obstruction of the oropharynx during sleep while the tongue muscles are relaxed. The natural movement of the tongue into the oropharynx can be prevented by the wire and elements coupled to the wire that resist the tongue's weight but allow the subject to swallow any saliva generated at any time. The wire and the elements coupled to the wire can be specifically formed, positioned, and/or connected to minimize invasiveness and patient discomfort while maximizing the hold on at least a portion of the tongue. The OSA prevention appliance can be removed in the morning and cleaned with methods similar to those used for false teeth. With as many advantages as the OSA prevention appliance has exhibited, however, the OSA prevention appliance has yet to reach a wide swath of the population. This is largely because each OSA prevention appliance must be designed and customized specifically for each patient with no standard method to follow. In other words, when a custom device is needed, several iterations tested over time are often required before a long term custom device is properly executed to a patient. Accordingly, a universal and improved method is described herein that can be used to design and customize OSA prevention appliances by one or more components of a system 100. Notably, the method (executed by the one or more components of the system 100) is universal (e.g., for a plurality of users) but the OSA prevention appliances produced according to the method are customized for specific users (of the plurality of users).

A key concept of the method (executed by one or more components of the system 100) is to extract and process information from multiple imaging modalities (e.g., imaging modality 1 102 and imaging modality 2 104) to create a custom OSA prevention appliance to treat and/or prevent OSA for each patient. At least two imaging modalities are each required to provide one or more high-resolution images in order to correctly model and make parts of the custom OSA prevention appliance. In the system 100, imaging modality 1 102 and imaging modality 2 104 are shown and described, but it will be understood that more/different imaging modalities may be used. Imaging modality 1 102 can be in electrical communication (wired and/or wireless) with the modeling system 106 to send 3D image(s) to the modeling system. Imaging modality 2 104 can also be in electrical communication (wired and/or wireless) with the modeling system 106. In some instance, a reconstruction system 105 can be between the imaging modality 2 104 and the modeling system 106 to convert a plurality of two-dimensional images taken by the imaging modality 2 into a three-dimensional reconstruction. In other instances, the reconstruction system 105 can be integrated into a portion of the modeling system 106 and/or into imaging modality 2 104 such that the plurality of two-dimensional or a 3D reconstruction are sent to the modeling system 106. The modeling system 106 can be in electrical communication (wired and/or wireless) with a manufacturing system 108 for creating each of the customized OSA prevention appliances from models created within the modeling system. Each of the imaging modality 1 102, imaging modality 2 104, optional reconstruction system 105, modeling system 106, and manufacturing system 108 can include at least one processor (not shown) and a non-transitory memory (not shown), and may include additional components such as user interfaces, displays, audio components, and any other circuitry common for implementation (e.g., power, communication, etc.). In some instances, one or more of the components of FIG. 1 can utilize the same and/or different processor and/or memory (which can be local and/or remote) and/or be embodied within a single unit.

For example, as shown in FIG. 1, the method executed by the system 100 involves extracting and processing information from multiple imaging modalities (imaging modality 1 102 can provide one or more 3D image(s) and imaging modality 2 104 can provide a plurality of two-dimensional images and can go through a reconstruction process, in some instances by reconstruction system 105, to provide a three-dimensional reconstruction) to create a custom, tightly fitted OSA prevention appliance for each patient. For example, imaging modality 1 102 can be an imaging modality capable of taking a three-dimensional oral scan, which can include a three-dimensional image of at least a portion of the patient's teeth and gums. The imaging modality 1 102 can be, for example, an intraoral scanner (e.g., intraoral light scanner, "IOLS"). The three-dimensional images including at least a portion of the patient's teeth and gums can be sent to the modeling system 106. The imaging modality 2 104 can be a device capable of taking a plurality of two-dimensional images of at least another portion of the oral cavity and at least a portion of an oropharynx including soft tissue. For example, the imaging modality 2 104 can be a curved beam computed tomography system and a three-dimensional reconstruction of at least a portion of the oral cavity can be created (e.g., optionally by reconstruction system 105) based on the curved beam computed tomography (CBCT) images that shows the anatomical position of the soft tissue of the tongue/oropharynx/airway boundary relative to a location of the patient's teeth. While every patient is different in exact results of the imaging, every patient does have at least one teeth and gums. Accordingly, based on the three-dimensional image of the teeth and gums and the three-dimensional reconstruction of at least portions of oral cavity and oropharynx, the modeling system 106 can identify and determine design parameters for each custom OSA prevention appliance for each respective patient.

The modeling system 106 can receive at least two different image types (e.g., the three dimensional images from Imaging modality 1 102 and the three-dimensional reconstruction from the plurality of two dimensional images from the imaging modality 2 104), including at least partially different portions of the patient's oral cavity and/or oropharynx, including hard and/or soft tissues. The modeling system 106 can combine the different image types to form a comprehensive picture (e.g., 3D image) of each given patient's anatomy and can create a model of an OSA prevention appliance customized for each given patient. The modeling system 106 can then pass the model of the OSA prevention appliance to the manufacturing system 108 that can create the customized OSA prevention appliance hardware. As noted, at least two image types from different imaging modalities are taken of different portions of the patient's anatomy, combined, transformed, and processed (as described in more detail below) before a model of the OSA prevention appliance can be created (as described in more detail below). The model of the OSA prevention appliance is manufactured to become a hardware OSA prevention appliance that is fully customized for the user and ready for use to at least partially prevent, treat, and/or alleviate OSA.

Figure 2:
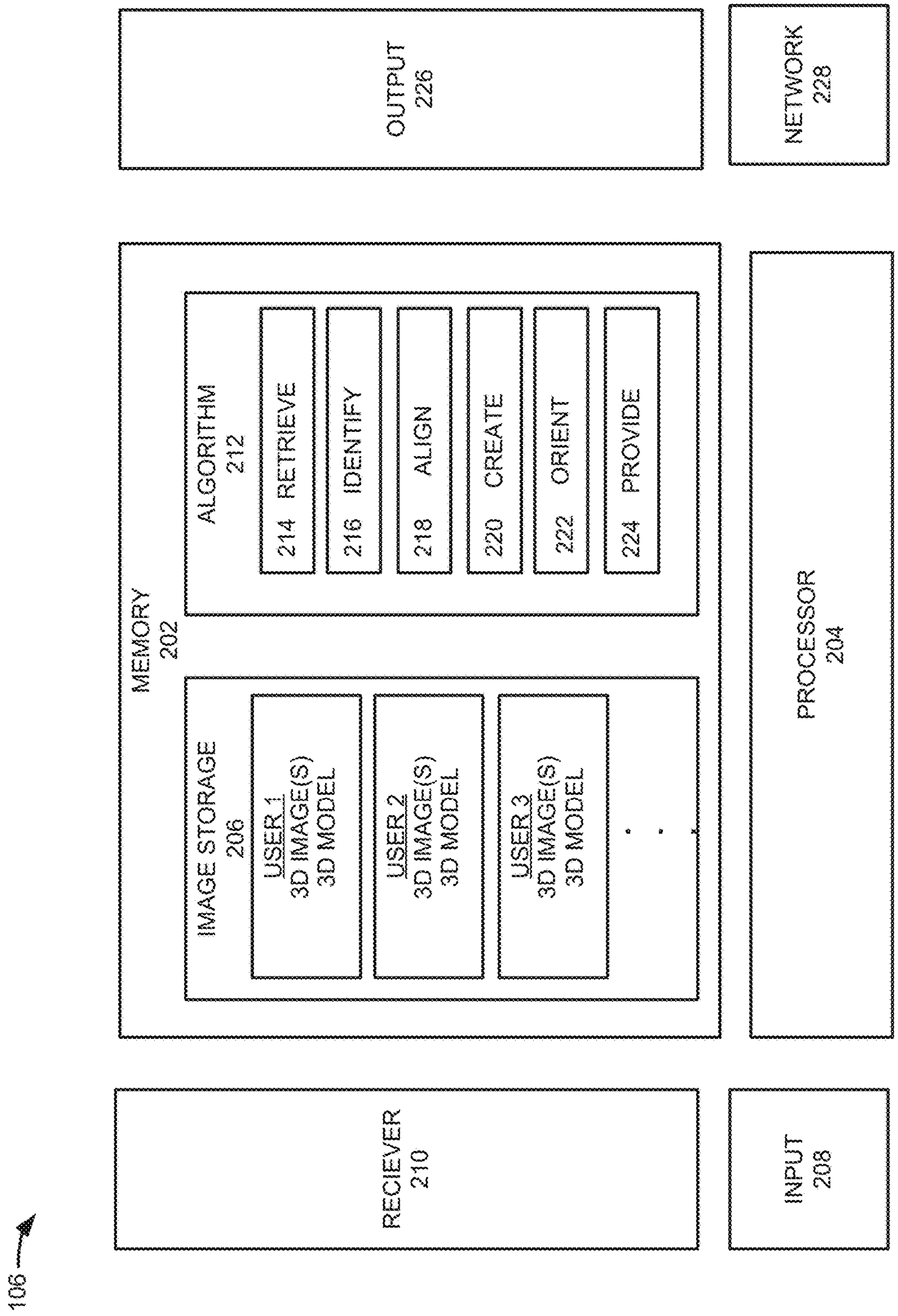
FIG. 2 is a block diagram showing an example of the modeling system of FIG. 1.

The modeling system 106 is shown in greater detail in FIG. 2. The modeling system 106 can include a memory 202 and a processor 204 and may include one or more of an input 208 (to communicate with a user interface such as keyboard, a mouse, a microphone, or the like), a receiver 210 (to receive data related to a given user), an output 226 (to provide the output model to the manufacturing system 108) and a network 228 (to communicate with the manufacturing system 108). Each of the components of modeling system 106 can be elements with at least a portion embedded in hardware. The memory 202 can store instructions (algorithm 212) and/or data (image storage 206). Although the image storage 206 is shown as storing data for three users (user 1, user 2, user 3 . . . ), it will be understood that the image storage 206 can include data from any number of one or more users (e.g., limited by memory size, file size, and storage constraints). For example, data for one user (or a subset of users) may be stored locally, but data for the other users (a greater number of users) may be available in a remote memory storage (e.g., a secondary memory that may be local and/or remote). Image storage 206 can include at least the three-dimensional image(s) and at least one of the models, once constructed (e.g., of at least a portion of the anatomy, of at least a portion of the OSA prevention appliance, etc.), for each user.

Further, the algorithm 212 can include steps that can be executed to produce an accurate model of an OSA prevention appliance specific for a user. The memory 202 can be accessed by the processor 204 and at least a portion of the image data retrieved from image storage 206 for one user and at least a portion of the algorithm 212. The processor 204 can execute the algorithm incorporating the retrieved data for the user. It should be noted that the image data (e.g., 3D image(s) and 3D model from a specific user) can be specific to the given user, but the algorithm can be standard for different users. As an example, the algorithm can include retrieving 214 (the two or more images, which can be three dimensional), identifying 216 (common points between the two or more images), aligning 218 (the two or more images), creating 220 (the three dimensional model), orienting 222 (three dimensional cylinder models and placing the three dimensional cylinder models within the three dimensional model), and providing 224 (the model of the three dimensional cylinders placed within the three dimensional model can be used to create a model of the OSA prevention appliance, which can be used to create the hardware OSA prevention appliance). Each of the steps of different algorithms are discussed in more detail below.

Described herein are two examples of different methods (employing versions of algorithm 212) that the system 100 can undertake to design the customized OSA prevention appliance for a specific patient. However, it should be understood that these methods are not exclusive and other methods can be used and still be within the scope described herein. Each method can receive and use the at least two types of images of different at least portions of the patient's oral cavity and/or oropharynx (e.g., the 3D image and the 3D reconstruction (or the plurality of two-dimensional images used to form the reconstruction), which can together make up 3D volume imaging data) from each imaging modality (e.g., image modality 1 102 and imaging modality 2 104). As shown in 300 of FIG. 3, three-dimensional oral scan data from imaging modality 1 (e.g., 102), which can include at least a portion of the teeth and gums (e.g., a portion of the oral cavity, and CBCT scan data showing reconstructed bone from imaging modality 2 (e.g., 104) can both be input into the modeling system and can be primed for alignment and combination. The CBCT scan data can be a plurality of two-dimensional slices data (e.g., images) of the patient's head that can be reconstructed into a three-dimensional reconstruction of the bone (e.g., teeth, mandible, lower palate, etc.) as shown.

Figure 4:
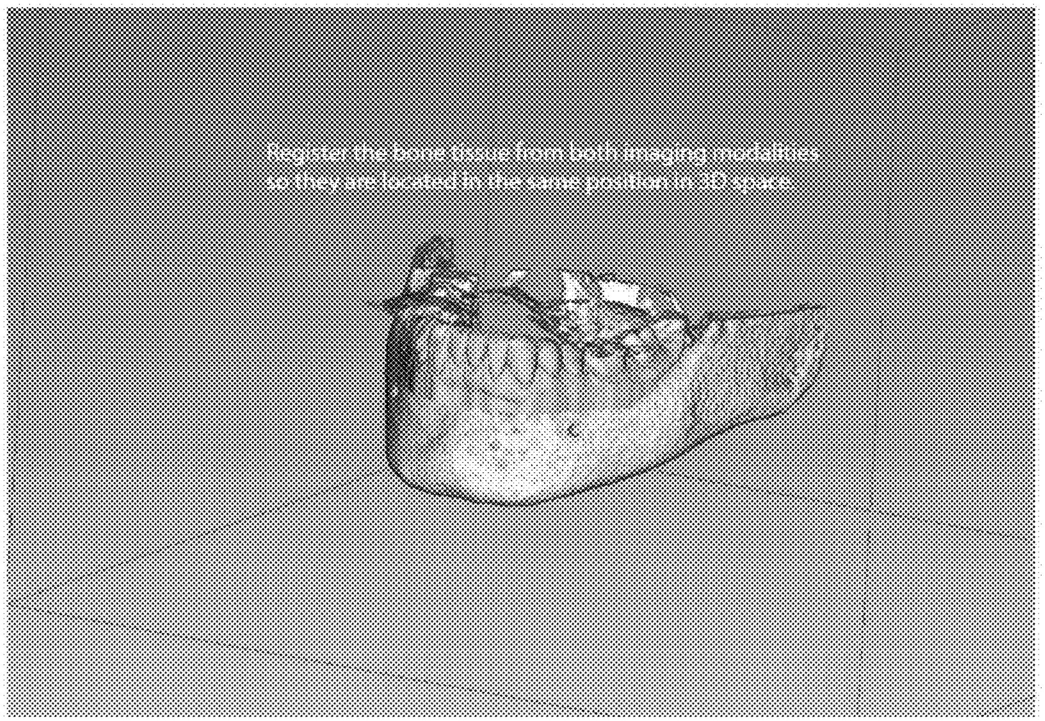

As shown in 400 of FIG. 4, the reconstructed bone (e.g., the three-dimensional reconstruction of at least a portion of the oral cavity and oropharynx) and the three-dimensional image(s) of the oral scan including the teeth and gums from both imaging modalities can be registered together such that they are located in the same position in 3D space. The aligned and registered model of the anatomy can provide a more accurate and precise model of the user's anatomy than could be made with data from a single imaging modality as each of the imaging modalities can better capture different types of tissues and/or structures. In some instances, the oral scan data can provide a more detailed image of the teeth than what exists in the CBCT scan and the CBCT scan can provide a more detailed image of the mandible and deeper interior portions of the oral cavity and/or portions of the oropharynx. The oral scan data can, for example, be higher resolution than the CBCT volume data, and this process allows the higher resolution oral scan data to be within the CBCT volume data so that the OSA prevention apparatus can be sized and positioned precisely for a user's exact teeth, oral cavity, and/or oropharynx features.

Figure 5:
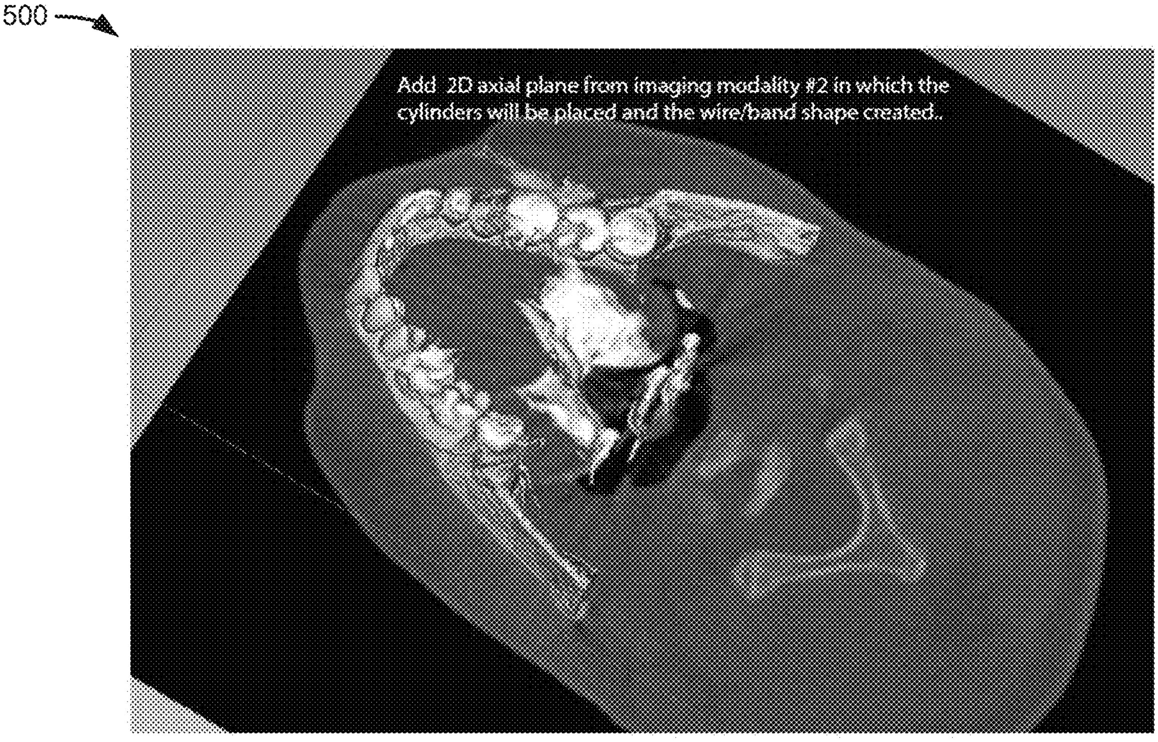
Figure 6:
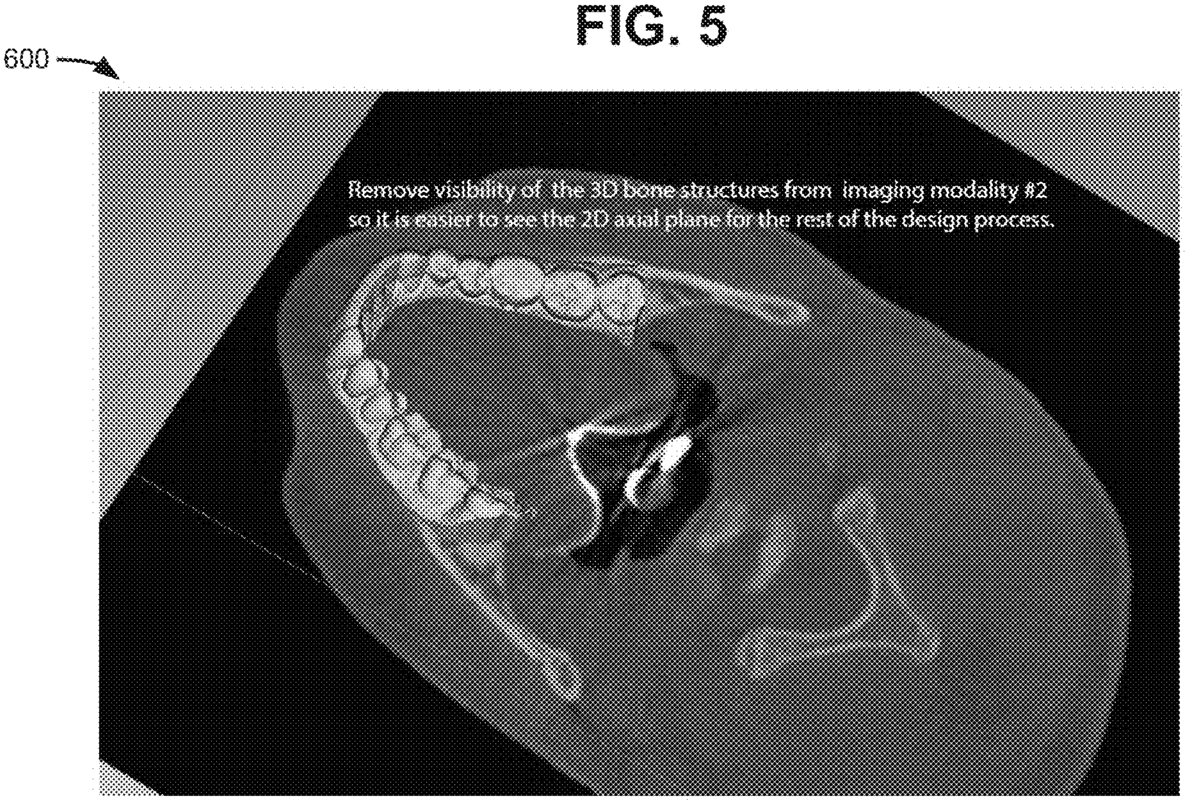

In 500 of FIG. 5, the model of the patient anatomy (e.g., including the data of additional anatomical features and a general shape of the user's head) is shown in a 2D axial plane, the additional anatomical features and general shape of the user's head can be added from the plurality of two-dimensional image scans of imaging modality 2. The added two-dimensional slice in the axial plane can include the tongue-airway boundary, which can be a critical design component. The axial plane can be the plane on which cylinders will be placed and the wire/band shape created for the model of the OSA prevention appliance. The axial plane can be chosen as described later. In 600 of FIG. 6, the visibility of the 3D bone structures from imaging modality 2 can be hidden from view to more easily visualize the teeth and gums with respect to the 2D axial plane for the rest of the modeling process.

Figure 3:
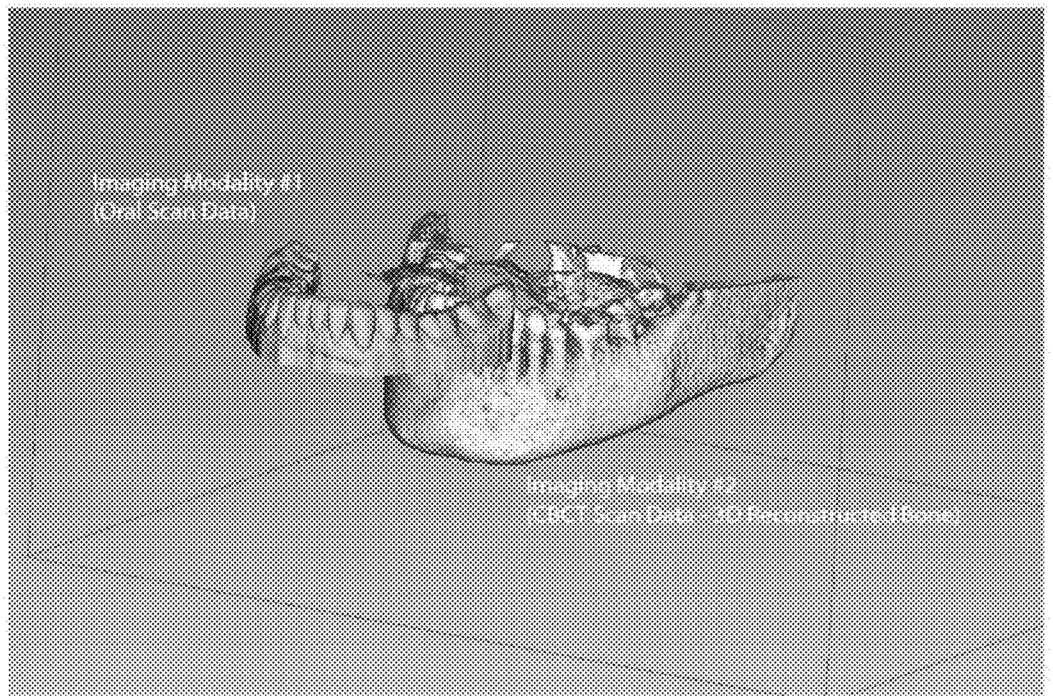
FIGS. 3-6 show example illustrations of modeling steps for merging images taken with the different imaging modalities of FIG. 1.

When system 100 executes the first method to customize an OSA prevention apparatus for a user, imaging modality 1 102 can take an oral scan of the subject's mouth that is saved as an STL file (e.g., in image storage 206 of memory 202) and imaging modality 2 can take a CBCT scan that can take a plurality of images of the user's oral cavity including the mandible that can also be saved as a CBCT file and reconstructed into three dimensions (the reconstruction can also and/or additionally be saved as a CBCT file). In the CBCT file for a given patient, the plane of the mandible can be identified and aligned horizontally. The volume can be re-segmented in the case that the user's head was tilted during the CBCT scan (e.g., the head can be "un-tilted"). The oral scan can be input and loaded with the CBCT scan (e.g., the two images loaded together are shown in FIG. 3). At least two matching points can be identified on the teeth and/or gums of the user within the oral scan and the CBCT. In some instances, three matching points can be identified.

The matching points can be used to register the oral scan with the CBCT in three dimensions (shown in FIG. 4). The system 100 can align the digital images to orient and place two cylinders within the CBCT volume in an axial plane that is ideal for retaining the tongue out of the airway.

The axial plane can be determined using the combination image. A sagittal plane at the medial location of the head can be identified, as illustrated in 704 of FIG. 7. A location of the apex of the tongue (e.g., the most posterior portion of the tongue in the sagittal plane) can be determined at Pt, shown in FIG. 7, element 702. And a horizontal axial plane containing the point Pt in the sagittal plane can be determined, the axial plane is shown as the horizontal line in FIG. 7, element 702). It should be noted that Pt refers to the apex of the tongue where the tongue is most posterior in the airway, is a critical design point, and lies in the sagittal plane in the medial location of the head. The point Pt is critical for design of the OSA prevention appliance because the wire must be placed on the axial plane including Pt.

Figure 7:
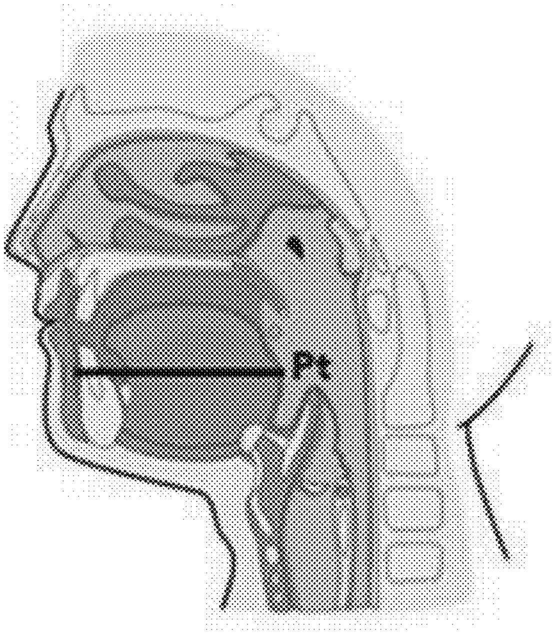
FIGS. 7-15 show example illustrations of modeling and manufacturing steps for customizing an OSA prevention appliance according to a first universal and improved method.
Figure 7:
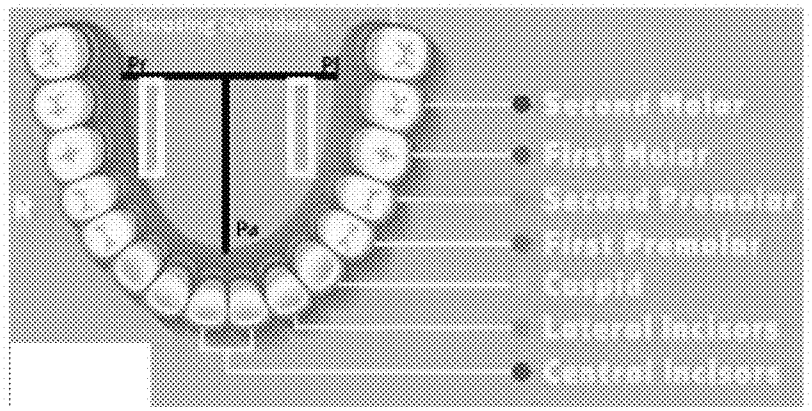

Once the axial plane is located, the locations of at least the first, second, and third molars on the left and right mandible can be identified, as shown in the illustration 704 of FIG. 7. It should be understood that these points can be identified in the combined image 600 if FIG. 6 and an illustration is used for ease of description and view. Points between the second and the third molar can be identified within the axial plane on both the left and right mandible (Pl and Pr, respectively, on FIG. 7, element 704). Other places for the points can be chosen depending on the user's anatomy. For example, if the third molar is missing on either side, points can be chosen between the second molar and the first molar. Similarly, if the second molar is missing on either side, points can be chosen between the first molar and premolar. A line connecting the two points Pl and Pr within the plane can be identified (shown as a horizontal line in FIG. 7, element 704). A point can be identified on the maximally anterior portion of the mandible on the midline (point Pa, shown in FIG. 7, element 704). Points Pt and Pa lie in the same sagittal plane (shown as the vertical line in FIG. 7, element 704), which is positioned at the midline of the head.

Models and/or representations of two threaded housing cylinders can be positioned on a plane that includes points Pa, Pl, and Pr (shown in FIG. 7, element 704). The models and/or representations of the two cylinders can be oriented in the anterior-posterior direction so that they are parallel to each other. The posterior ends of each of the models and/or representations of the two threaded housing cylinders can be on the line from Pl-Pr. Each of the models and/or representations of the two cylinder can be laterally translated within the Pa-Pl-Pr plane until the anterior end of the cylinder is located within a specified distance from the mandible. The models and/or representations of the two cylinders are shown in element 802 of FIG. 8 merged into the combined image on the axial plane from 600 of FIG. 6. The models and/or representations of the two cylinders remain parallel to each other and are oriented in the 3D space along with the teeth and the CBCT data containing the tongue outline and airway edge. At least the representation of the teeth and gums of the user with the models and/or representations of the two cylinders can be model merged and the merged file can be entered into an appliance design application of the modeling system (e.g., 106) (shown in, e.g., FIG. 8, element 804). The above steps can lead to the design of the custom components (e.g., the splint, wire, and saddle), as described in detail below, that are used to create a fully assembled OSA prevention appliance that can be worn by a user for the prevention and/or treatment of OSA that can be created and customized for each user.

From here, all of the remaining components of the OSA prevention appliance can be determined for the specific user anatomy. It should be noted that the further steps can be conducted by the modelling system 106 and/or the manufacturing system 108. It should be noted that the modeling system 106 and the manufacturing system 108 may be different programs but embedded on the same or different computing devices.

Figure 8:
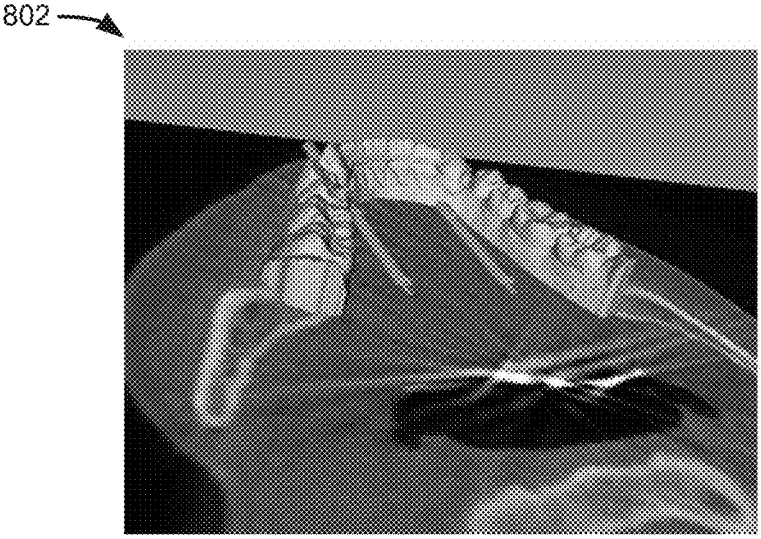
Figure 8:
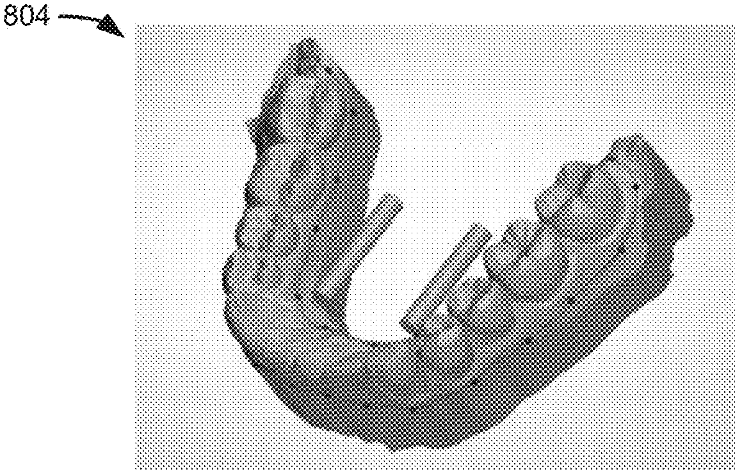
Figure 8:
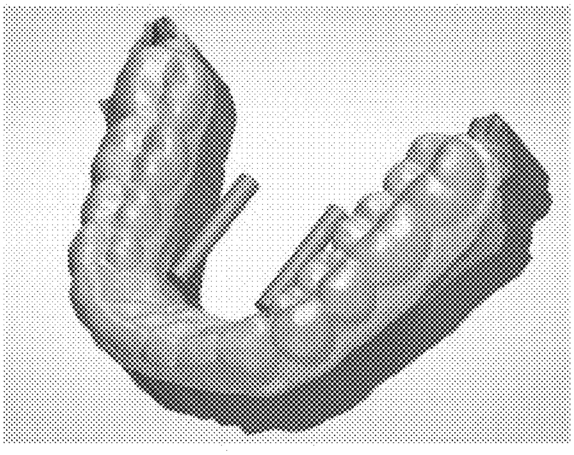
Figure 9:
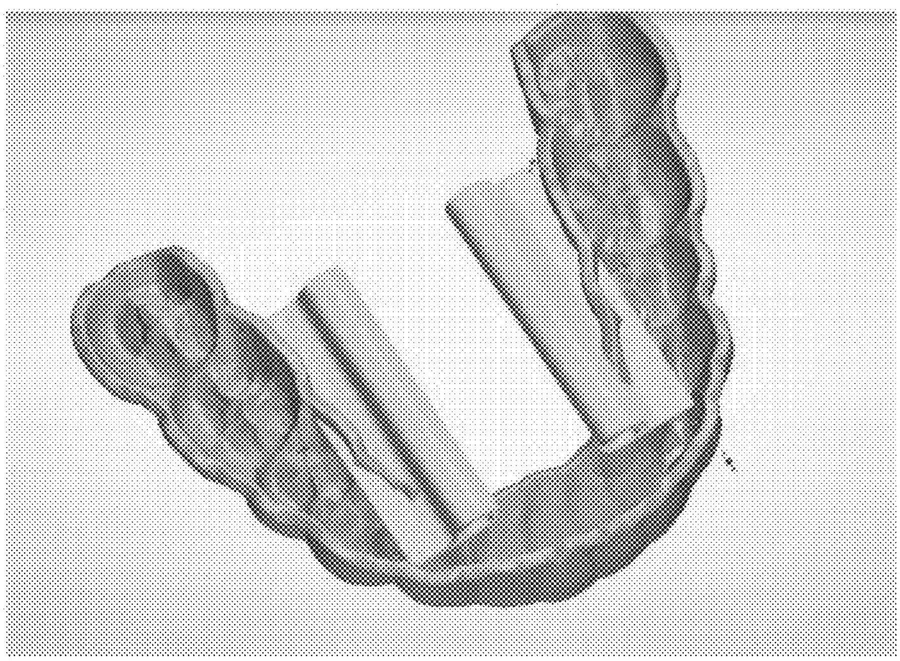
Figure 9:
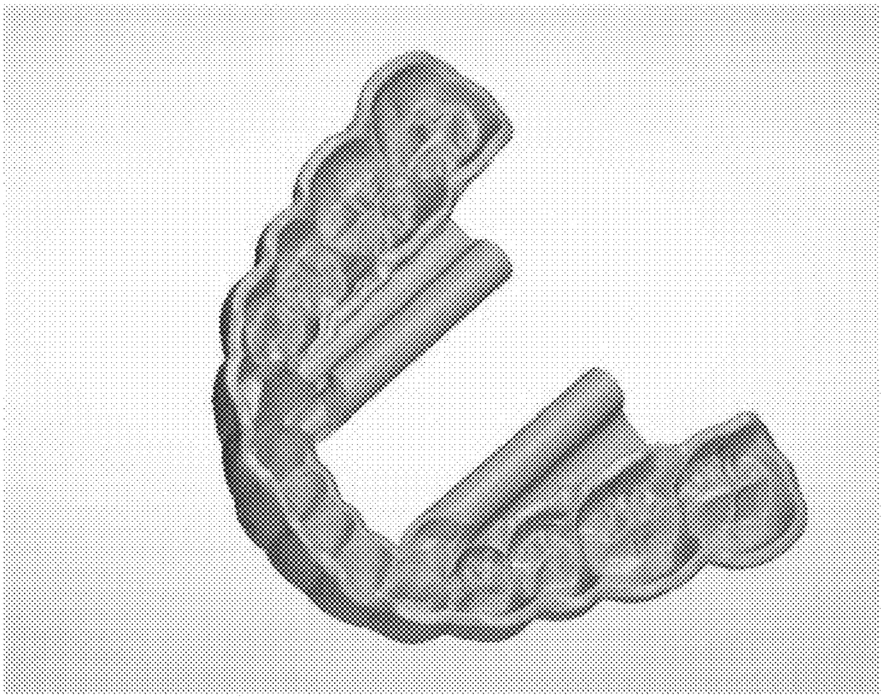

The model of the teeth, gums, and two cylinder housings of element is shown in element 804 of FIG. 8. Using the location of the two model cylinders in reference to the model of the teeth and gums from the digital oral scan data, the teeth and gums can be identified and a spline line can be created around the gums near the teeth as shown in element 804 of FIG. 8. The spline line can define lower bounds for a model of a splint (of the mouthguard). The model of the splint (of the mouthguard) can be modeled over at least the teeth to the spine line as shown in FIG. 8, element 806. The splint can be created to the exact measurements of the user's teeth. As shown in element 902 of FIG. 9, the splint (of the mouthguard) can then be removed from the model of the teeth and gums and model wing attachments (e.g., rectangular planes) connecting each of the models of the cylinders to the respective lingual sides of the splint can be added. The models of the wing attachments can be added by extending a rectangle toward to the respective lingual sides of the splint (of the mouthguard) in the axial plane of the splint until the posterior edge contacts the respective lingual sides of the splint. Any excess material (e.g., that overlaps with the splint (of the mouthguard)) can be removed from the model based on subtracting the wing attachment material from the model of the splint based on the digital oral scan data of the teeth. The model of the mouthguard including the splint over the teeth, the two cylinder housings, and the wings attaching the cylinder housings to the splint are shown in FIG. 9, element 904. The completed model of the splint can be sent to the manufacturing system 108 and can be output as an STL file and sent out for three dimensional printing) so that the model constructed as shown in FIG. 9 can be output as an actual three dimensional printed portion of the OSA prevention appliance that can be worn by the user.

Figure 10:
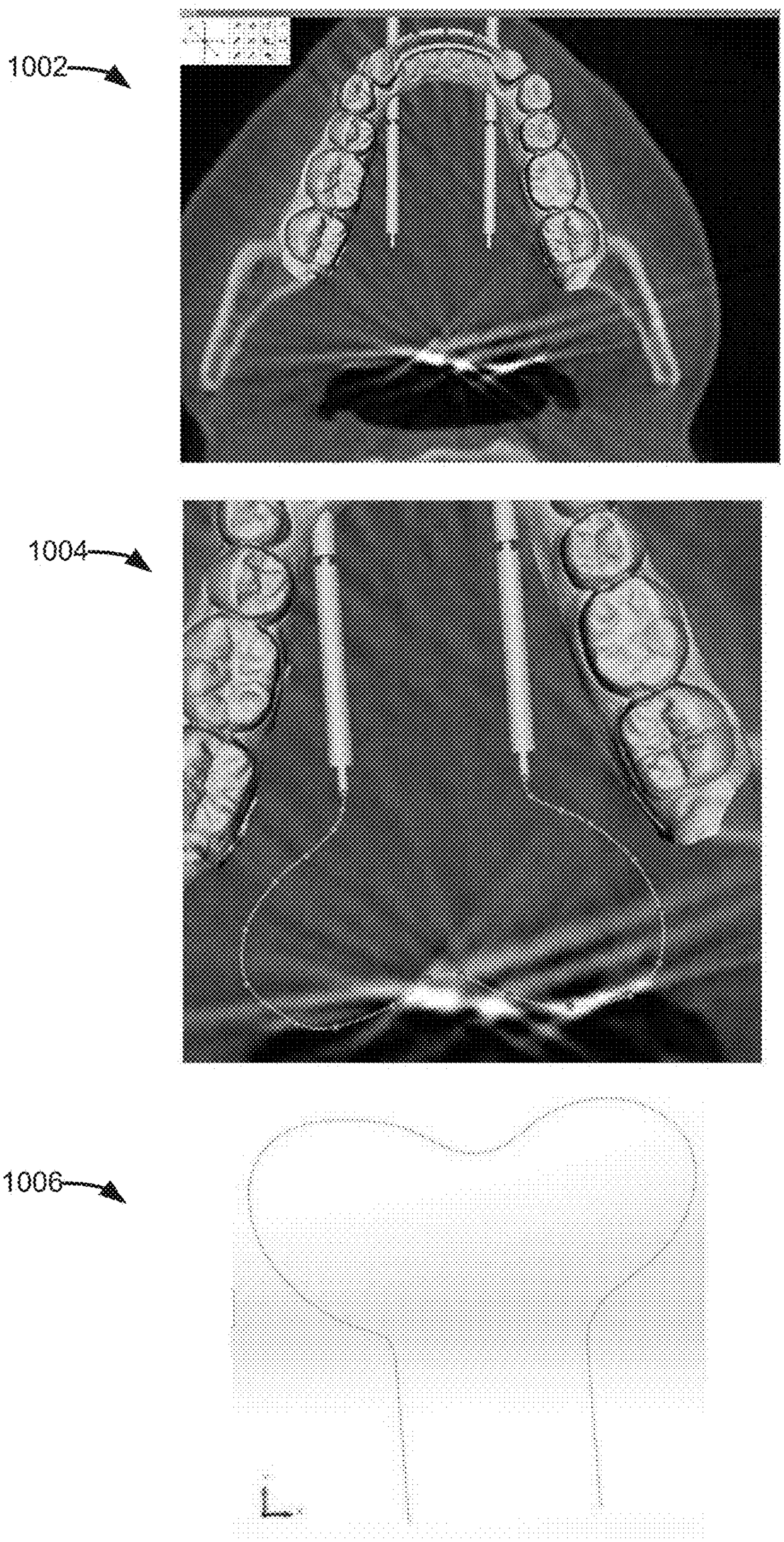

FIG. 10 shows the modeling of the wire/band portion of the OSA prevention appliance used to hold the tongue. FIG. 10, element 1002 shows the model of the splint (of the mouthguard) over the teeth and a precursor for the cylinder housings in the CBCT axial plane (from element 600 of FIG. 6). Utilizing the CBCT axial slice image of the plane the wire can be positioned along with the models of the housing cylinders in the plane. A model of a continuous wire can be positioned along with the model housing cylinder placement within the plane. The model of a continuous wire shape can haven an end extending from within one of the models of the cylinders and out into the mouth keeping a specified distance from the mandible and also utilizing edge detection to trace along the outline of the posterior surface of the tongue and airway until the other end of the wire reaches a location inside the model of the opposite cylinder (shown in FIG. 10, element 1004). The shape of the wire between the ends can be a saddle shape (as shown), an arc, or any other shape that can hold the weight of the collapsed tongue during sleep while minimizing discomfort of the user. The completed model of the wire, shown in FIG. 10, element 1006, can be output into a file format that can be accepted by a wire bending machine so that the model of the wire constructed as shown in FIG. 10 can be output as an actual shaped wire configured to mate with the three-dimensional printed portion of the OSA prevention appliance that can be worn by the user.

Figure 11:
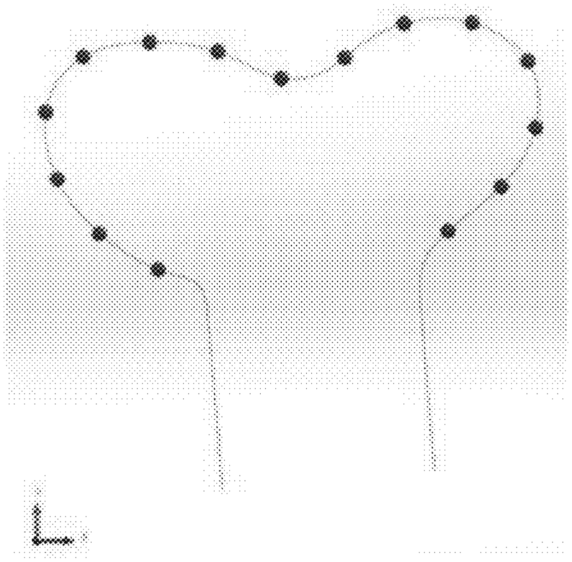
Figure 11:
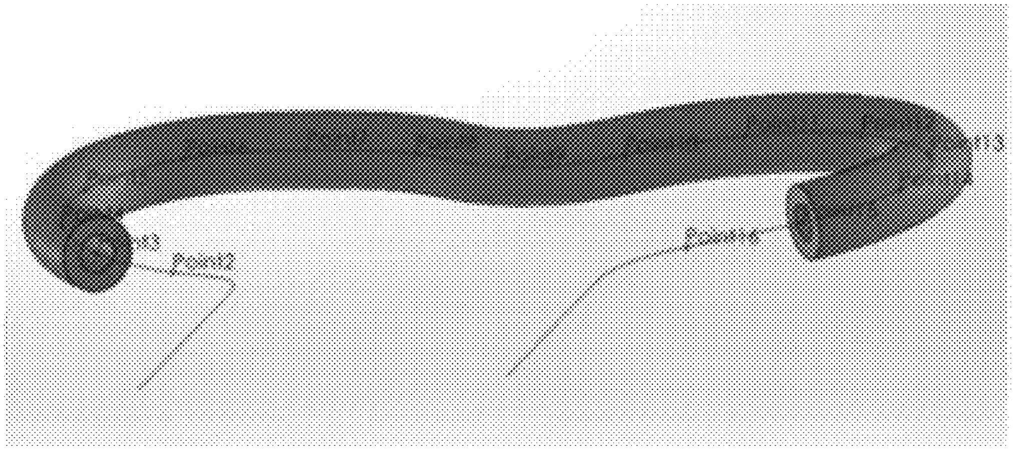

The OSA prevention appliance can, in some instances, include an attachment (e.g., a saddle or tongue retention attachment) that can surround at least a portion of the wire and provide additional comfort and/or stabilization to the tongue. Utilizing the wire shape model of FIG. 10, element 1006, the saddle or tongue retention attachment can be designed. As shown in FIG. 11, element 1102 at least the curved portion of the wire model can be divided into equal segments. For example, fifteen points can be equally spaced around the curved portion of the wire model. Using the point locations that are a given distance in (e.g., two in the fifteen point example shown) from each side of the straight ends of the wire, a cylindrical attachment model can be created between the chosen around the wire model and following the wire shape. FIG. 11, element 1004 shows the completed tongue retention model with an annular cross section for receiving the wire. The model of the tongue retention model can be designed as annular or can be hollowed out in an additional step not shown. This model of the cylindrical attachment can be cut in half using the plane where the wire is positioned as a reference to create an upper and lower half of the attachment model. These two models can be saved and sent out to be three dimensionally printed or otherwise manufactured (so that the two models can guide the three-dimensional printer). The two models can be designed such that they can be reattached together.

Figure 12:
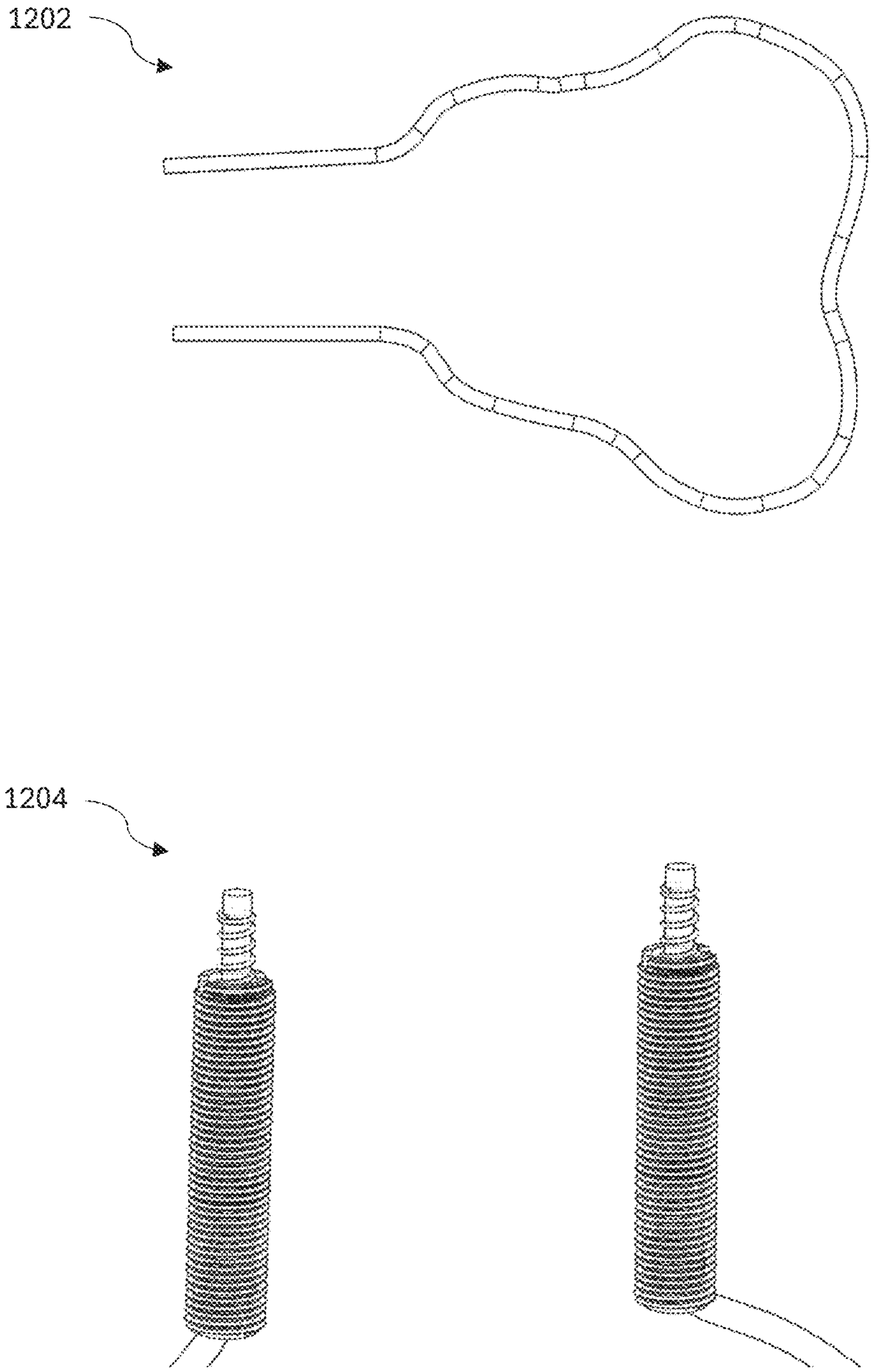
Figure 13:
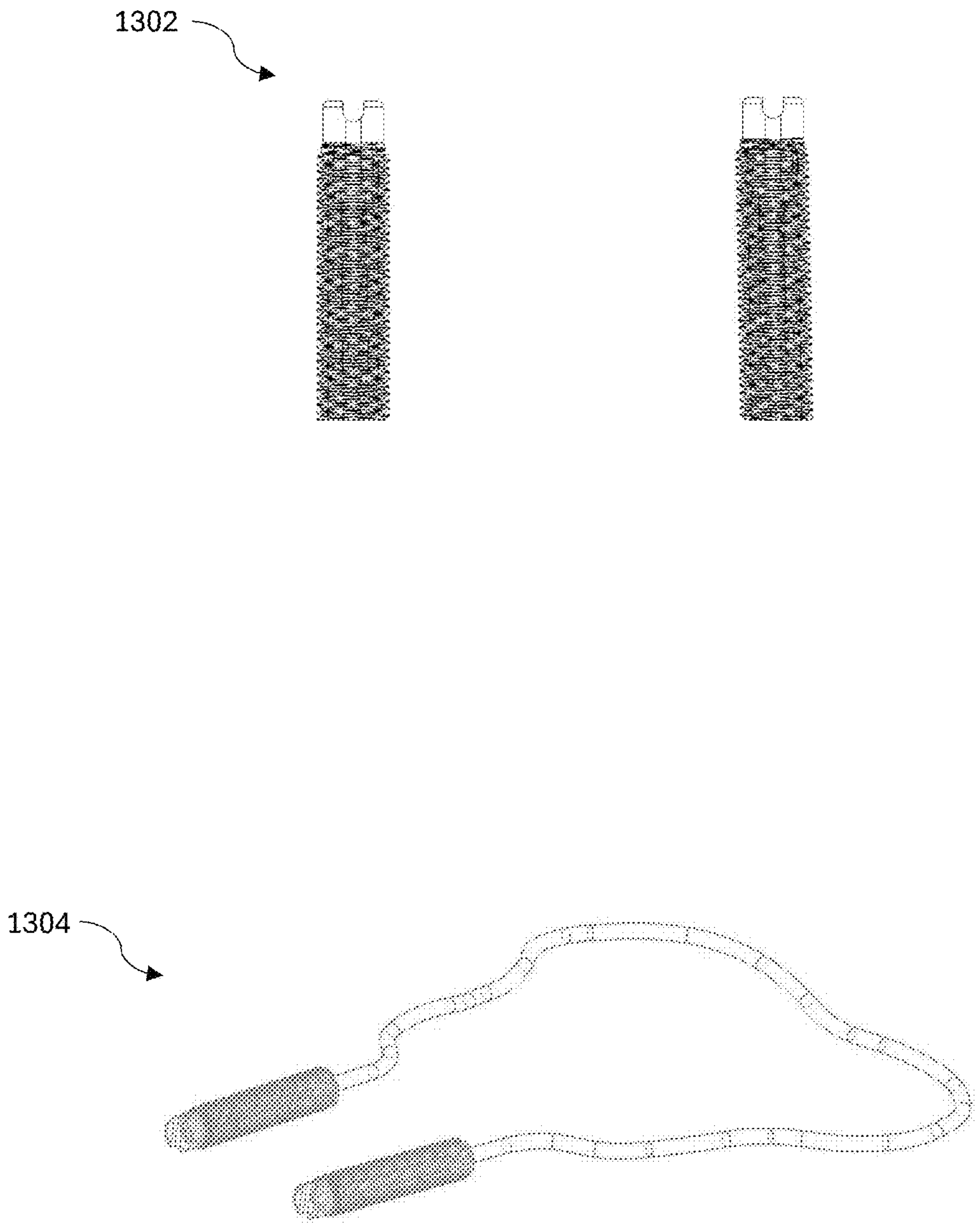

The wire subassembly can be created by manufacturing system 108. A wire can be custom bent, e.g., a 1.2 mm diameter wire, based on the user's anatomy as determined in FIGS. 10 and 11 above (shown in FIG. 12, element 1202) (e.g., using the manufacturing system 108). Threaded housing components and then springs can be placed around the straight wire ends (shown in FIG. 12, element 1204). The springs can be between the wire and the threaded housing components. The threaded housing components can have an exterior diameter configured to fit within the model of the housing cylinders. The springs can have a given spring constant (e.g., that can assist the wire in holding the weight of the tongue, but still allow swallowing). Then, washers can be placed on the wire ends and laser spot welded to each end of the wire respectively. The washers can hold at least the springs on the wire. A thread cap can then be inserted into the open end of the threaded housing (e.g., screwed in) and a 360° laser weld can be performed to join the threaded housing and thread cap pieces together (shown in FIG. 13, element 1302). A completed hardware wire subassembly is shown in FIG. 13, element 1304 with the shaped and bent wire, the springs, the washers, the threaded housings, and the thread cap end pieces.

Figure 14:
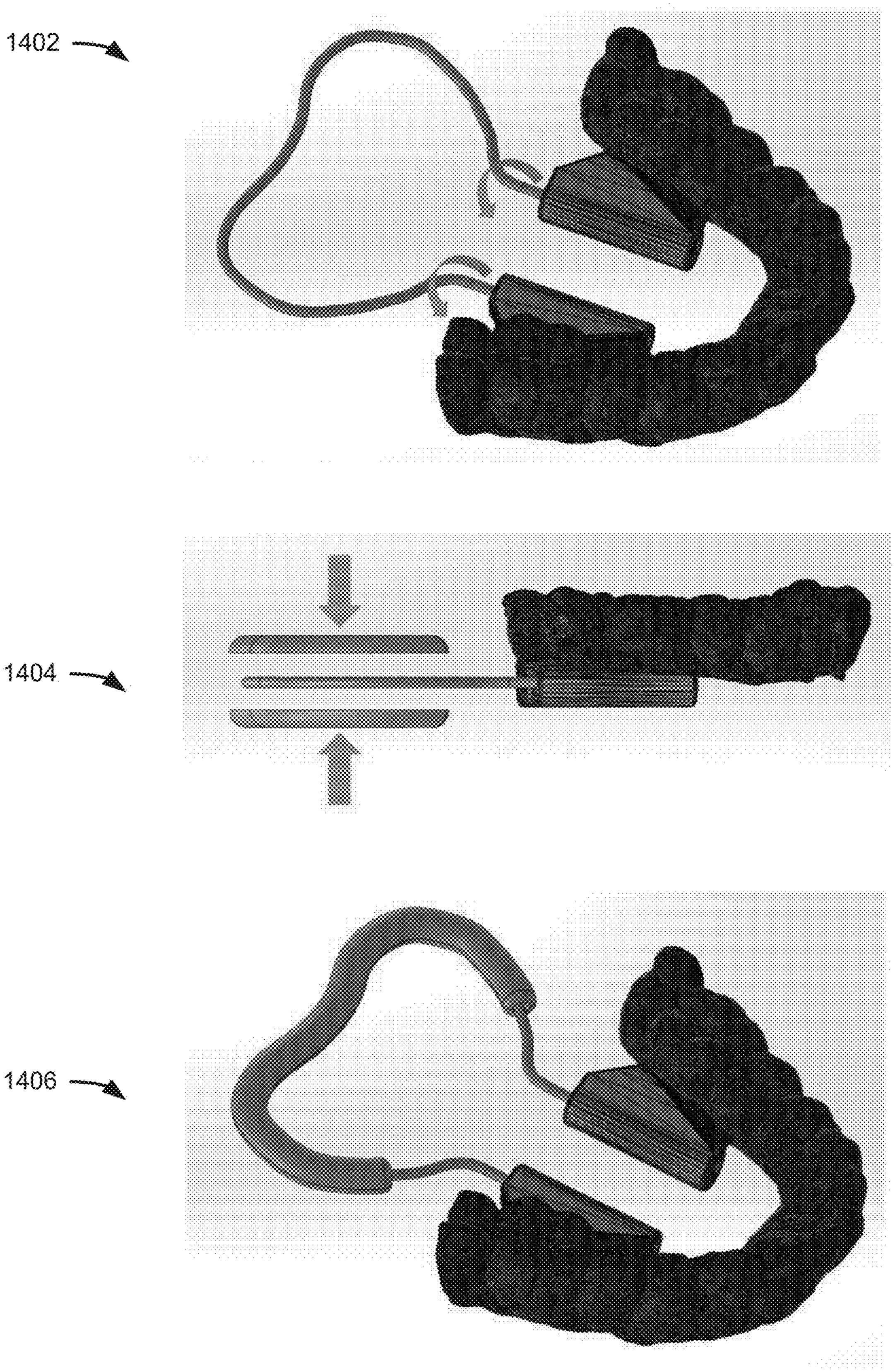
Figure 15:
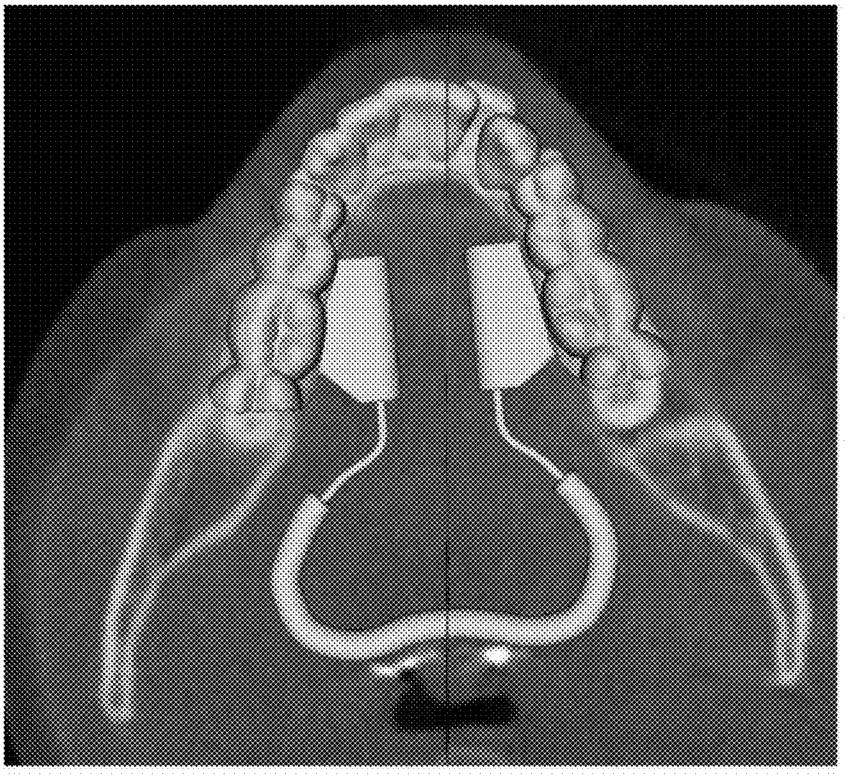
Figure 15:
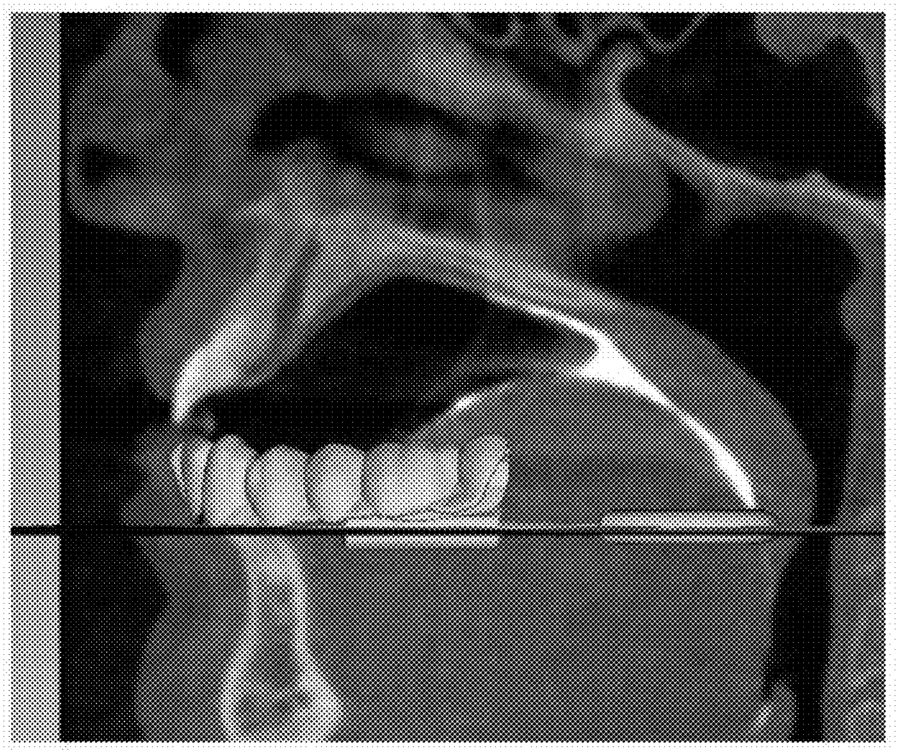

FIG. 14 shows illustrations for final steps in completing a customized OSA prevention appliance. In FIG. 14, element 1402, the wire sub assembly can be screwed into the housing cylinders attached to the mouthguard. The housing cylinders can also be threaded. The wire subassembly can be threaded into the housing cylinders until the threaded housings are completely within the housing cylinders. In FIG. 14, element 1404, the two halves of the tongue retention structure components can be attached to the wire. The optional tongue retention attachment can be positioned by closing the two halves around the wire and connected the halves (e.g., connecters, adhesive, heat, etc.). FIG. 14, element 1406 shows a completed example custom OSA prevention appliance where the mouthguard can be removable fitted over the user's lower teeth for use and removed in the morning and the wire, including the optional tongue retention attachment can be positioned to hold the tongue from collapsing into the oropharynx during sleep. FIG. 15 elements 1502 and 1504 show different CBCT scan views of a completed OSA prevention device positioned within a user's mouth.

The second method variation for creating the custom OSA prevention appliances will be described. It will be understood that methods other than the two described can be used and are within the scope of this disclosure. The steps for determining the specific anatomy of the given user are similar to those described with respect to the first method variation When system 100 executes the second method to customize an OSA protection device for a user, system 100 can implement steps described above with respect to FIGS. 3-6. For example, imaging modality 1 102 can take an oral scan of the subject's mouth (e.g., a portion of the oral cavity including at least teeth and/or gums of a user) that is saved as an STL file and imaging modality 2 can take CBCT scans of at least a portion of the subject's oral cavity, including the mandible, and a portion of the oropharynx. The imaging modality 2 can be a CBCT that can take a plurality of two-dimensional images that can be combined to form a three-dimensional reconstruction of the at least the portion of the oral cavity and oropharynx. The modeling system (e.g., 106) can receive the three-dimensional oral scan, the three-dimensional reconstruction, and the two-dimensional CBCT scans. In the CBCT file for a given patient, the plane of the mandible can be identified and aligned horizontally. The volume can be re-segmented in case the user's head was tilted during the CBCT scan/reconstruction. The oral scan can be input and loaded with the CBCT scan/reconstruction (the two images loaded together are shown in FIG. 3). At least two matching points can be identified within the oral scan and the CBCT scan/reconstruction. In some instances, three matching points can be identified. The matching points can be used to register the oral scan with the CBCT in three dimensions (shown in FIG. 4). The system 100 can align the digital images within the CBCT volume in an axial plane that is ideal for retaining the tongue out of the airway (shown in FIG. 5). The three-dimensional bone structure (e.g., the mandible) can be hidden from view such that the axial plane, the gums, and the teeth remain visible (shown in FIG. 6).

Figure 16:
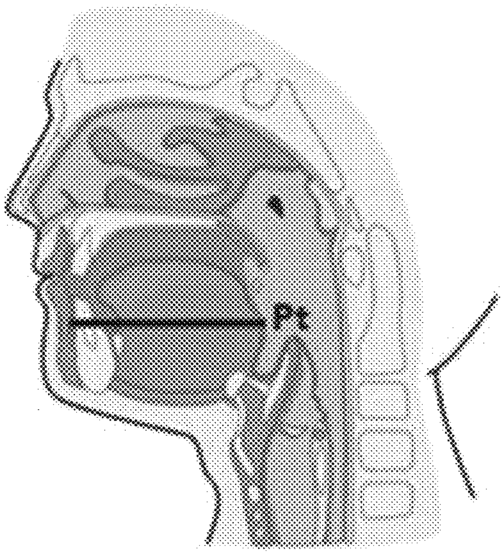
FIGS. 16-23 show example illustrations of modeling and manufacturing steps for customizing an OSA prevention appliance according to a second universal and improved method.
Figure 16:
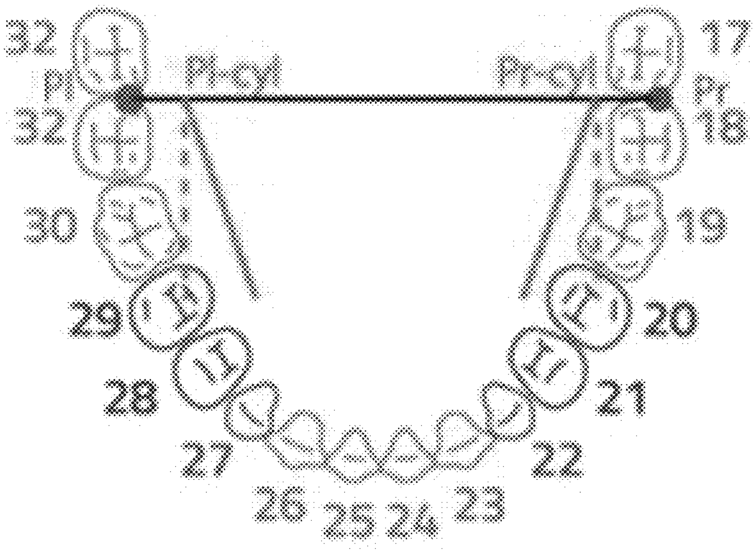

The combination image (with the bone structure no longer visible as in FIG. 6) can be used to determine the axial plane. A sagittal plane at the medial location of the head can be identified, as illustrated in FIG. 16, element 1602. A location of the apex of the tongue (e.g., most posterior portion of the tongue in the sagittal plane) can be determined as point Pt and the horizontal axial plane containing this point Pt, can also be determined shown in FIG. 16, element 1602). It should be noted that Pt refers to the point at the apex of the tongue where the tongue is most posterior in the airway, is a critical design point, and lies in the sagittal plane in the medial location of the head. The point Pt is critical for design of the OSA prevention appliance because the wire must be placed on the axial plane that includes Pt for the specific user.

Once the axial plane is located, locations of at least the first, second, and third molars on the left and right sides of the mandible can be identified, as shown in FIG. 16, element 1604. It should be understood that these points can be identified in the combined image 600 if FIG. 6 and an illustration is used for ease of description and view. Points between the second and the third molar can be identified within the axial plane on both the left and right sides of the mandible (Pl and Pr, respectively). Other places for the points can be chosen depending on the user's anatomy. For example, if the third molar is missing on either side, points can be chosen between the second molar and the first molar. Similarly, if the second molar is missing on either side, points can be chosen between the first molar and premolar. A line connecting the two points Pl and Pr within the plane can be identified (shown as a horizontal line in FIG. 16, element 1604). Points can be identified on the line that are a given distance (e.g., 4 mm) from any bone structure of the teeth/mandible on both sides (shown in FIG. 16, element 1604, as Pl-cyl and Pr-cyl). From each of points Pl-cyl and Pr-cyl a line (dashed lines) can be drawn that is perpendicular to the existing (horizontal) line and is a length (e.g., 18 mm) long, extends anteriorly toward the front teeth, and is completely within the sagittal plane that includes points Pl and Pr. From these lines (which can, as shown, intersect one or more teeth) an orientation of the model housing cylinders can be determined (e.g., to not run into any anatomical features) by rotating a number of degrees around Pl-cyl and Pr-cyl until the anterior ends of the line are a distance from the teeth/bone structures. As an example, point Pr-cyl can be fixed and the dashed line can be rotated clockwise until all the points on the dashed line are at a minimum distance of 4 mm from any bone structures. This example can be repeated for the left side to get point Pl-cyl; the perpendicular line can be rotated counter-clockwise until the 4 mm distance requirement is met. Once this is completed, the cylinder center line (solid line on angle) can be extruded onto a 3.0 mm diameter cylinder for the rest of the design. The extrusions can form the models of the threaded housing cylinders (also referred to as housing cylinders).

Figure 17:
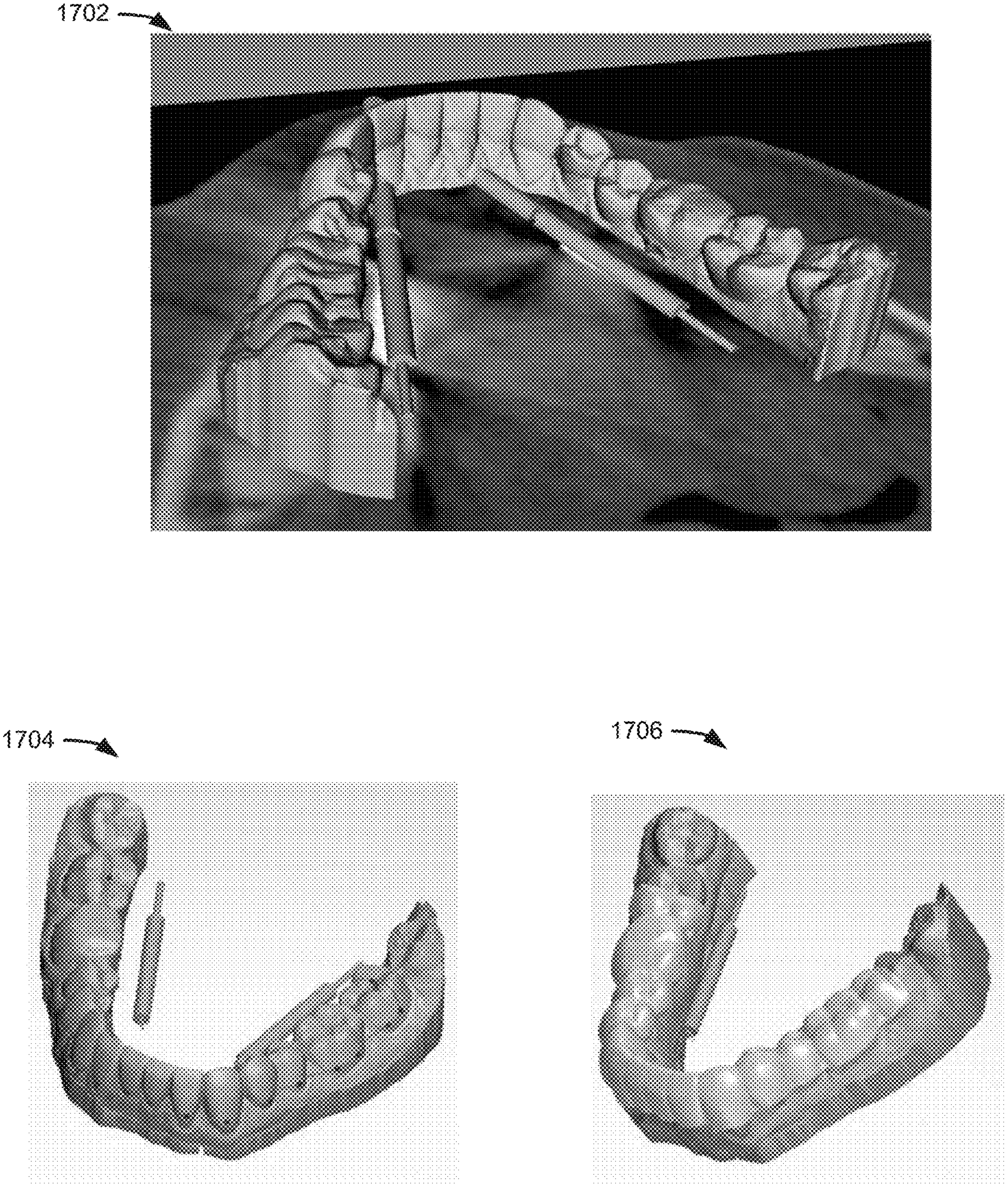

Models and/or representations of two threaded housing cylinders can be positioned on the sagittal plane that includes points Pl and Pr. FIG. 17, element 1702, shows the oral scan including at least the teeth and gums, the axial plane of the CBCT scan including the tongue and airway outlines/boundaries, and the model cylinders combined together. The model cylinders may be raw models (e.g., extending to a connection through the oral scan image of the teeth and gums) (as shown) which can be cut down to the length as described in FIG. 16. At least the representation of the teeth and gums of the user with the models and/or representations of the two cylinders can be model merged and the merged file can be entered into an appliance design application (shown in FIG. 17, elements 1704, 1706).

From here, all of the remaining components of the OSA prevention appliance can be determined for the specific user anatomy. It should be noted that the further steps can be conducted by the modelling system 106 and/or the manufacturing system 108. It should be noted that the modeling system 106 and the manufacturing system 108 may be different programs but embedded on the same or different computing devices.

Figure 18:
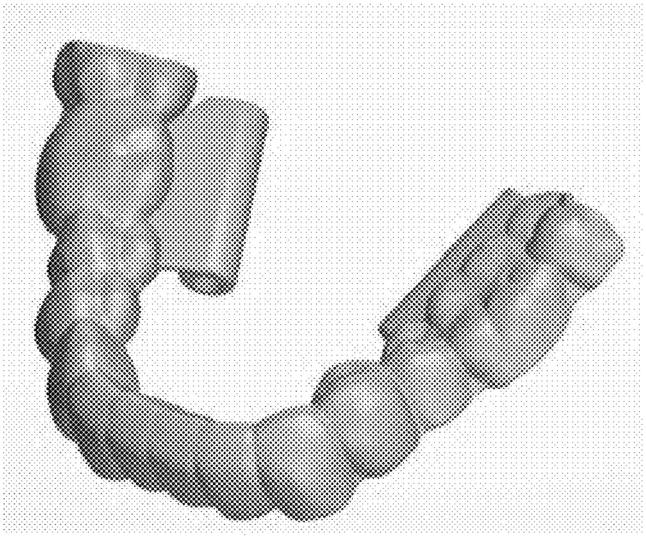
Figure 18:
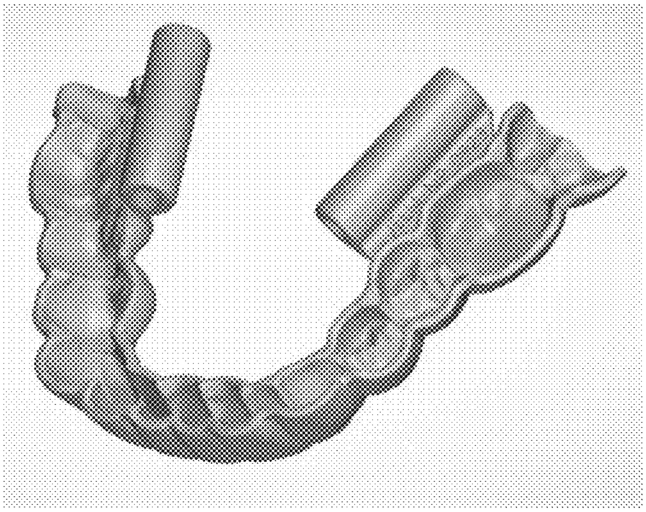

FIG. 17, element 1704, shows the models of the two cylinder housings are oriented at precise angles relate the teeth and gums. Using the location of the two model cylinders oriented in three dimensional space along with the digital oral scan data of the teeth, the teeth can be identified and a spline line can be created around the gums near the base of the teeth as shown in FIG. 17, element 1704. The spline line can define a lower bounds for a model of a splint (of the mouthguard). The model of the splint (of the mouthguard) can be modeled over at least the teeth to the spline line as shown in FIG. 17, element 1706. The splint of the mouthguard can be modeled to the exact measurements of the user's teeth (e.g., can include any specific user anatomy, missing teeth, etc.). As shown in FIG. 18, elements 1802 and 1804 (from different views) wing attachments can be extruded to connect the models of the housing cylinders with the respective lingual sides of the splint (of the mouthguard). Any excess material can be removed based on subtracting the wing attachment material from the digital oral scan data of the teeth. The completed model of the mouth guard, including the splint, the two housing cylinders, and the wing attachments can be output as an STL file and sent to the manufacturing system (e.g., 108) for three dimensional printing and construction of the OSA prevention appliance. Notably, the entire mouthguard portion of the OSA prevention appliance can be created to the exact measurements of the user's teeth, gums, etc. so that it is precisely the correct size for the user. Precision in the formation of the OSA prevention appliance improves user toleration.

Figure 19:
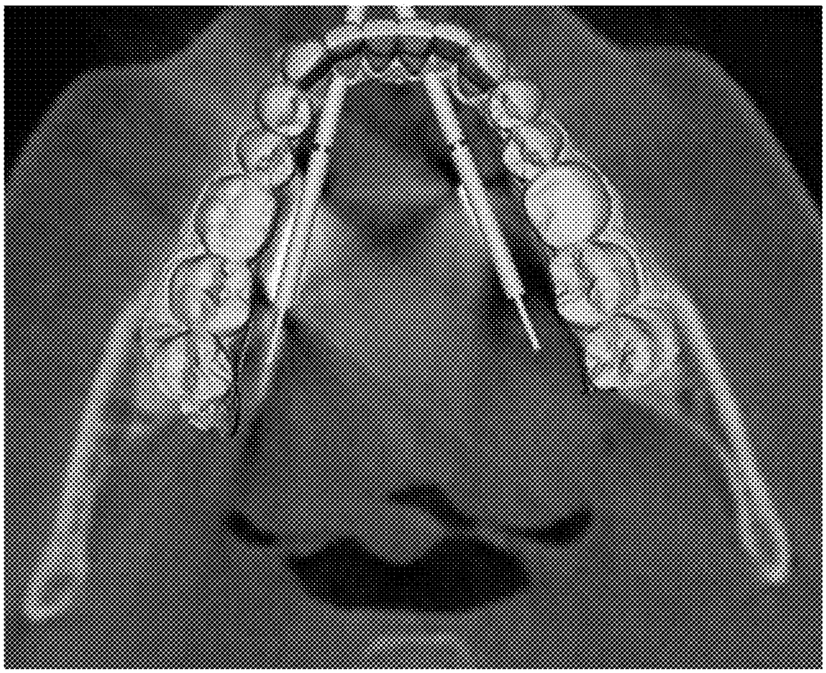
Figure 19:
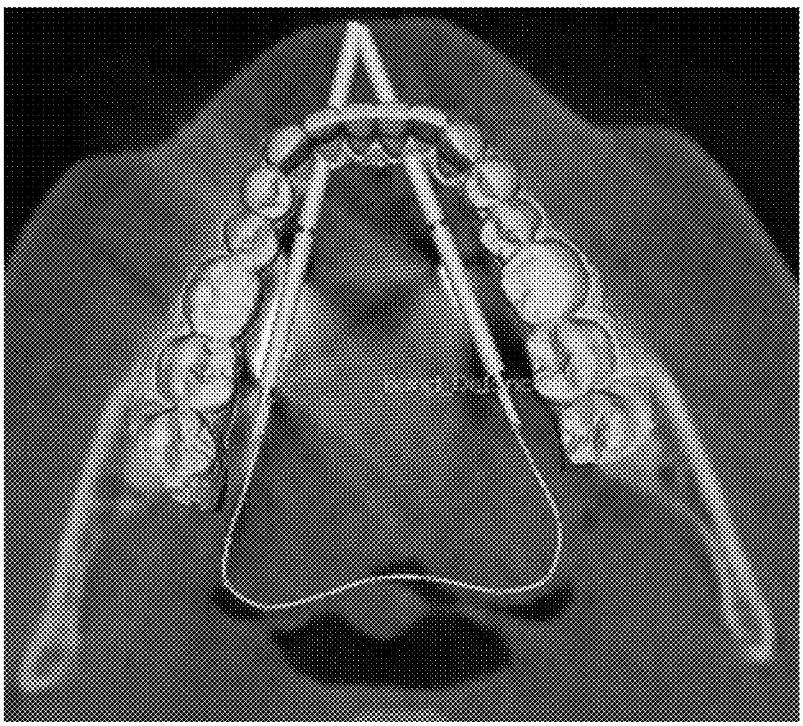

Referring now to FIG. 19, the wire portion of the OSA prevention appliance can also be modeled based on the user's anatomy. Utilizing the CBCT axial slice image of the plane the straight ends of the wire can be positioned along with the pre-cursor of the model of the cylinders in the plane as shown in FIG. 19, element 1902). The straight ends of the wire can be positioned to go through the center of the cylinder housings and extend a length (depending on the size of the user's mouth) in the axial plane. FIG. 19, element 1904 shows an example of the entire model wire starting from one straight end extending from a model of a cylinder housing out into the mouth, bending in a shape, keeping a specified distance from the mandible and also utilizing edge detection to trace along the outline of the posterior surface of the tongue and airway until the wire straightens (to the other straight end) and reaches a location inside the model of the opposite cylinder (shown in FIG. 19, element 1904).

Figure 20:
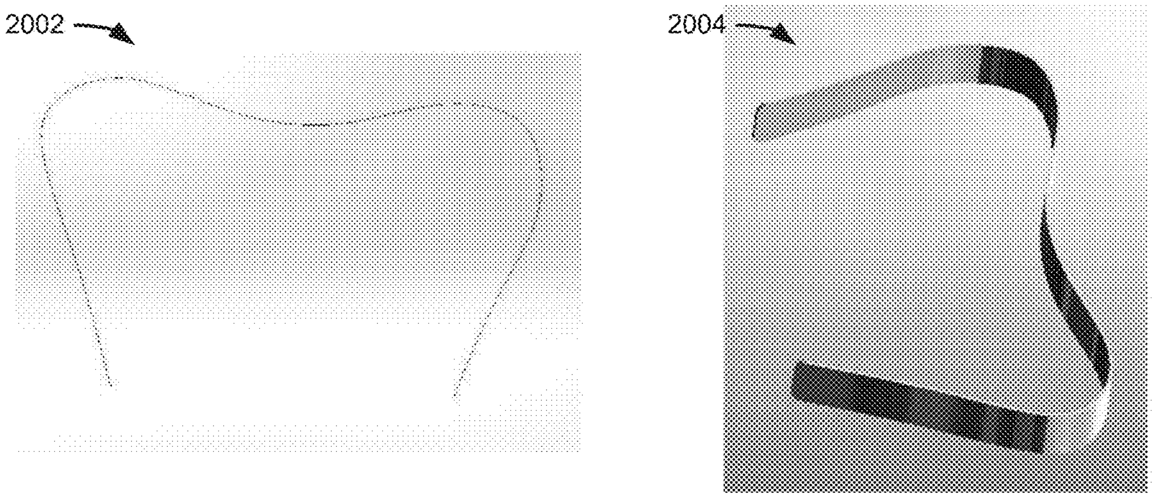
Figure 21:
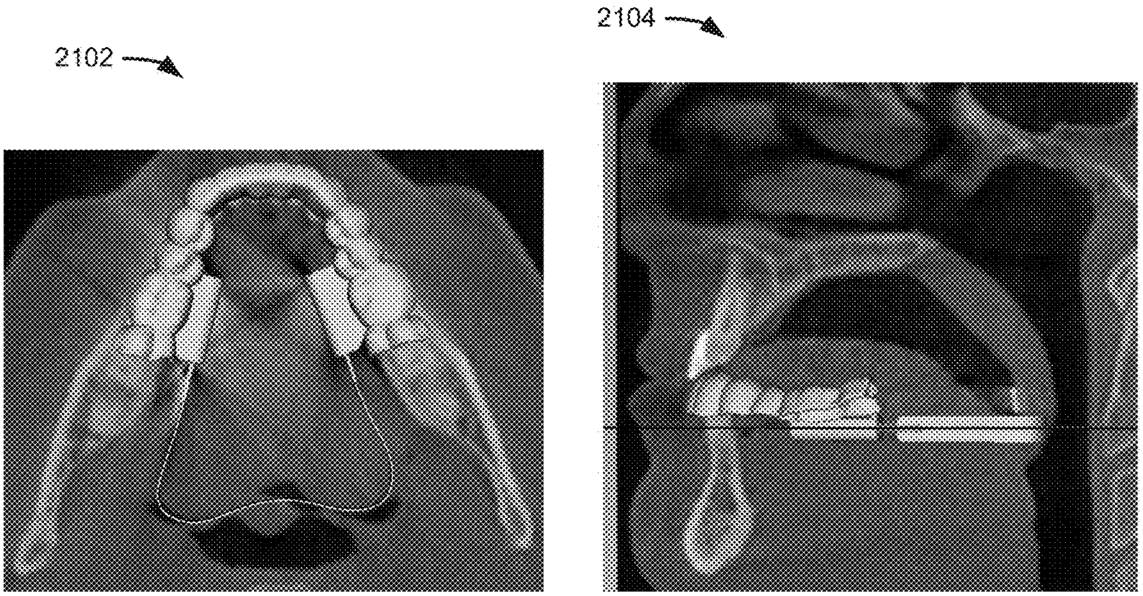

FIG. 20, elements 2002 and 2004 show example models of the intermediate portion of the wire (e.g., between the straight ends). It should be noted that the cross-sectional area of the wire can be any shape (e.g., circular, elliptical, rectangular, square, etc.) and/or dimensions, and can also be referred to as a band. The model of the wire can be shaped (custom bent) based on the user's anatomy (shown in FIG. 20, elements 2002, 2004). The shape of the band can be a saddle shape (as shown), an arch, or the like. The model of the band can be output into a file format accepted by a wire bending machine (e.g., of manufacturing system 108) so that the model of the wire can be output as an actual shaped band configured to mate with the three dimensional printed portion of the OSA prevention appliance that can be worn by the user. In some instances, the band can be thicker in the area near the oropharynx and thin down as it reaches the straight ends and the connection with the housing cylinders. In other instances, the thick band (e.g., the intermediate portion shown in FIG. 20, elements 2002 and 2004) can be welded to thin pieces (e.g., the straight ends) that connect to the housing cylinders (discussed further in the methods). Optionally, a tongue retention attachment, like that described above, can also be modeled and added to the band. FIG. 21, elements 2102 and 2104 show two different views of the combined model of the OSA prevent appliance with the split (of the mouthguard) having the wings and housing cylinders and the entire wire extending in the continuous shape from the housing cylinders in the axial plane toward the point at the posterior portion of the tongue and the boundary of the airway.

Figure 22:
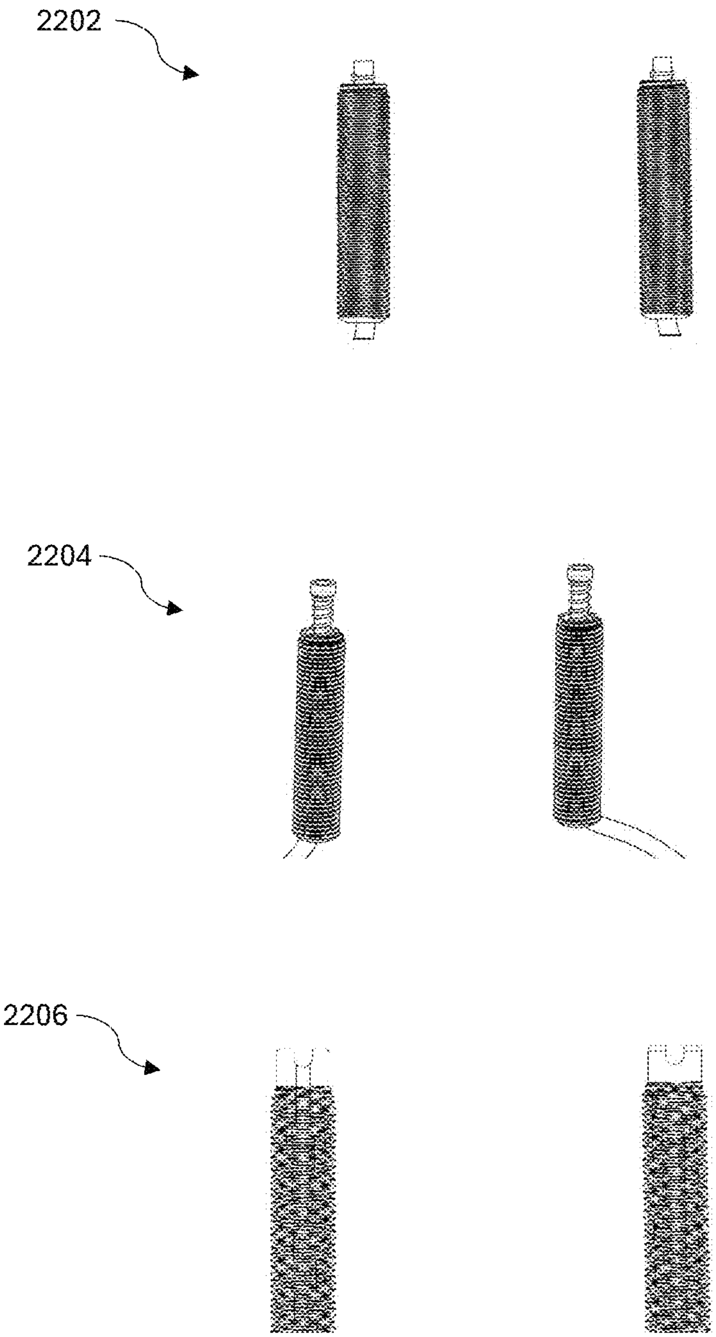
Figure 23:
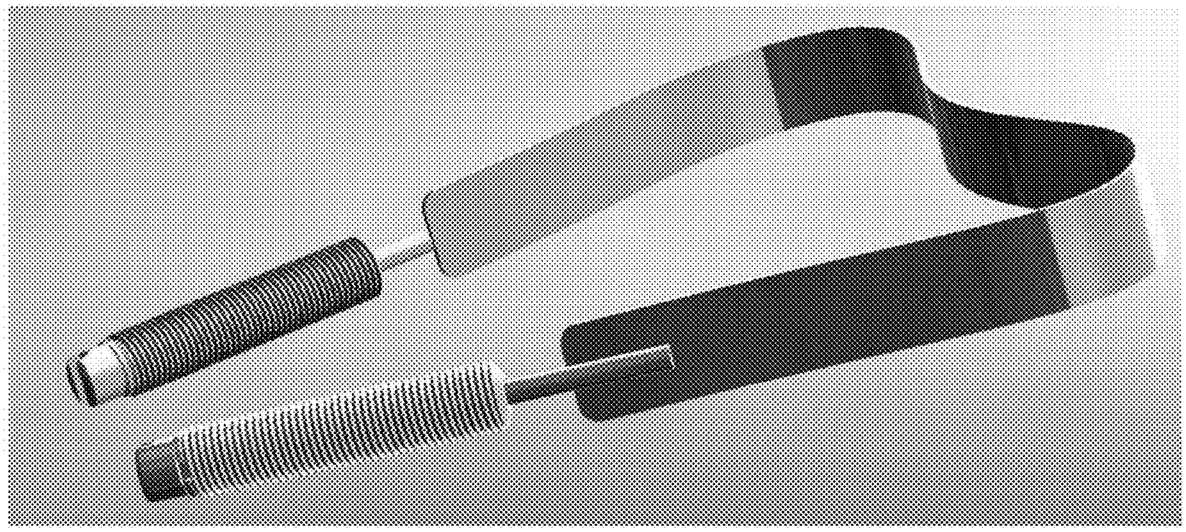
Figure 23:
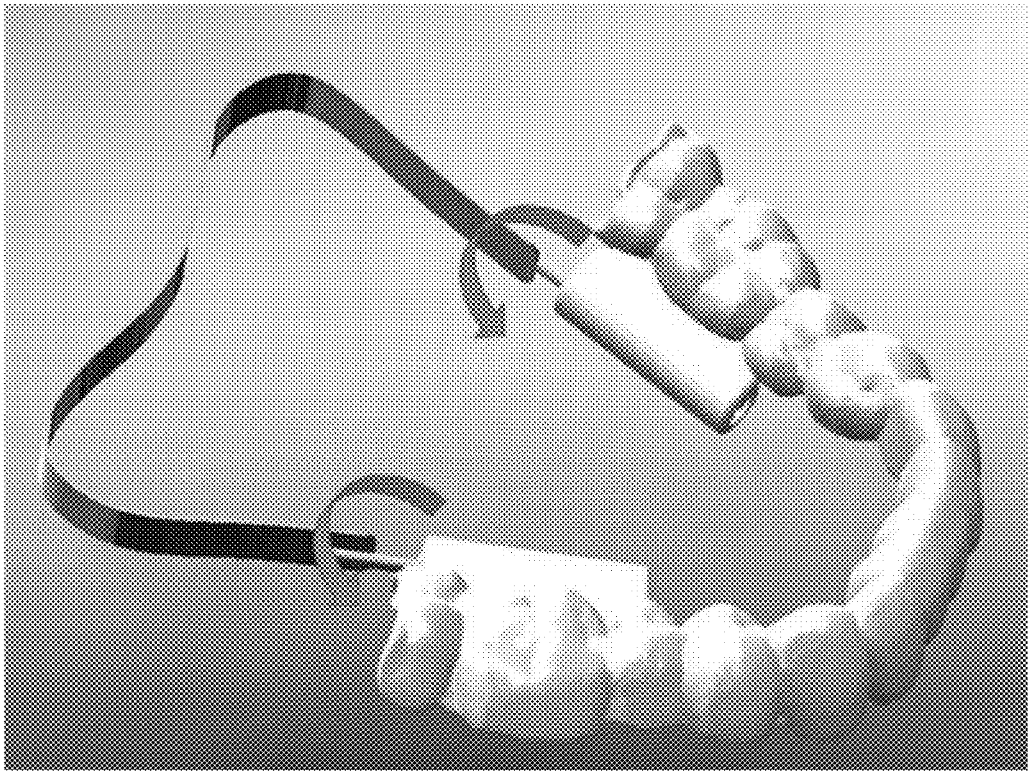

To connect the wire and the cylinder housings, the wire subassembly can be formed by manufacturing system 108. The wire (modeled in FIG. 20) can be bent based on the model and, if separate, the straight ends can be connected to the intermediate portion of the wire. FIG. 22, element 2202 shows threaded housing components and springs can be placed around the straight ends of the wire. The springs can be between the wire and the threaded housing components. The threaded housing components can have an exterior diameter configured to fit within the model of the housing cylinders. The springs can have a given spring constant (e.g., that can assist the wire in holding the weight of the tongue, but still allow swallowing). Washers are then placed on the wire ends and laser spot welded to each end (shown in FIG. 22, element 2204). The washers can hold at least the springs on the wire. A thread cap can be then inserted into the open end of each of the threaded housings and a 360° laser weld can be performed to join the threaded housing and the thread cap pieces together (shown in FIG. 22, element 2206). If not already connected to the intermediate portion of the wire the straight ends can be then welded to the custom bent band. FIG. 23, element 2302 shows a completed wire subassembly with the separate straight ends welded to the intermediate portion of the wire, which is shaped as a saddle with a rectangular cross section. FIG. 23, element 2304 shows the wire subassembly being screwed into the housing cylinders (which can also be threaded to fit the threaded housing to compete the OSA prevention appliance.

IV. Methods

Another aspect of the present disclosure can include methods (FIGS. 24-30) that provide a universal and improved way to customize an OSA prevention appliance for a user. The methods can be implemented, for example, by the system 100 of FIG. 1 with the modeling system 106 shown in FIG. 2 and the manufacturing system 108. As shown in FIG. 2, steps can be stored in a non-transitory memory 202 and are executable/executed by a processor 204.

For purposes of simplicity, the methods are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method, nor is the method necessarily limited to the illustrated aspects. Moreover, at least portions of different methods may be implemented together.

The OSA prevention appliance can be created for the specific anatomy of the given subject. For example, the OSA prevention appliance can be fitted to the subject's mouth so that the mouthguard fits tightly onto the lower teeth and the wire extends in a precise shape and to a precise position to stop the tongue from collapsing and blocking the oropharynx during sleep, while still giving the subject the ability to swallow. Notably, the OSA prevention appliance can prevent obstruction during sleep while the tongue muscles are relaxed from the lack of muscle tone. The natural movement of the tongue into the oropharynx can be prevented by elements coupled to the wire that resist the tongue's weight but allow the subject to swallow (e.g., springs, cylindrical holders, anchors, etc.).

Figure 24:
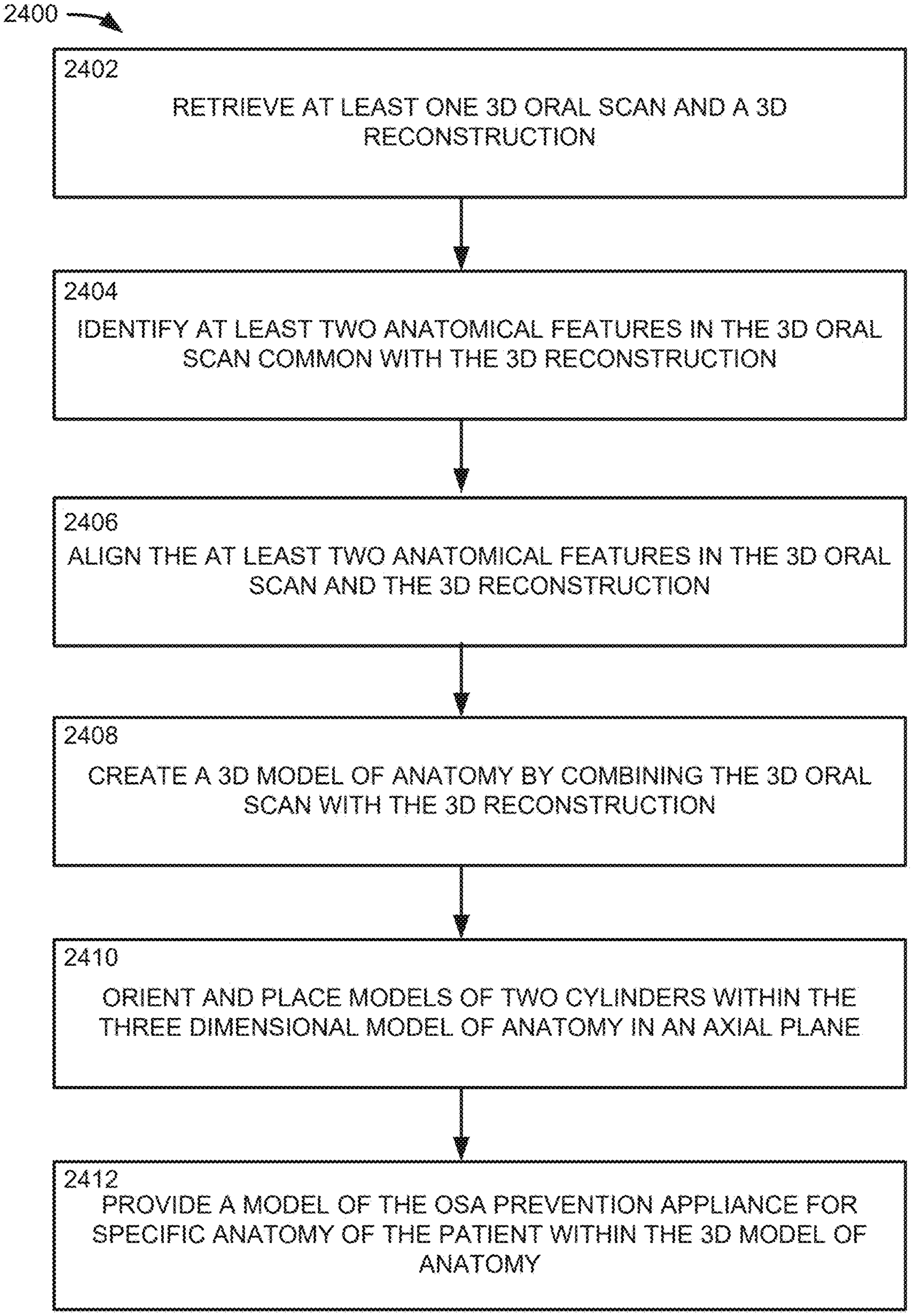
FIGS. 24-30 are process flow diagrams showing variations of universal and improved methods for customizing an OSA prevention appliance for a user.

Referring now to FIG. 24, illustrated is a method 2400 for creating an obstructive sleep apnea (OSA) prevention appliance for a subject. One or more steps of the method 2400 can be stored in the non-transitory memory and executable/executed by the processor (shown in FIG. 2) of the system shown in FIG. 1. At 2402, at least one three-dimensional oral scan and a three-dimensional reconstruction can be retrieved (e.g., from the non-transitory memory by the processor). Alternatively, the at least one three-dimensional oral scan and the three dimensional reconstruction can be received directly from the imaging modalities and simultaneously stored in memory. The at least one three-dimensional oral scan can include at least a portion of an oral cavity of the patient taken with a first imaging modality. As an example, the portion of the oral cavity can include at least a portion of the teeth and/or the gums (showing details of the teeth and/or the gums). The first imaging modality can be, for example, an intraoral scan. The three-dimensional reconstruction can be a combination of a plurality of two-dimensional images (e.g., scans) of at least another portion of the oral cavity and at least a portion of an oropharynx (e.g., from different positions around the user's head) taken with a second imaging modality. The second imaging modality can be, for example, a cone beam computer tomography (CBCT) scan. The other portion of the oral cavity and the at least the portion of the oropharynx in the three-dimensional reconstruction can include at least a portion of a mandible, at least another portion of the teeth, at least a portion of an interior of the patient's mouth, at least a portion of a tongue, and/or at least a portion of the oropharynx. The three-dimensional reconstruction can specifically include the boundaries of the airway and the tongue. The three-dimensional reconstruction can show dimensionality of the oral cavity and oropharynx without the specificity of detail of the oral scan. It should be noted that the second imaging modality (e.g., CBCT) generally is different from the first imaging modality (e.g., oral scan). Each type of imaging modality can include different details, tissues, and/or structures necessary for the creation of the custom OSA prevention appliances.

At 2404, at least two common anatomical features (e.g., specific teeth, bony structures of the mandible, or the like) can be identified in the three-dimensional oral scan and in the three-dimensional reconstruction. In some instances, two common anatomical features can be identified, but in other instances three or more common anatomical features can be identified. The common anatomical features can guide the alignment of the three-dimensional images. At 2406, the at least two anatomical features can be aligned to bring the at least one three-dimensional oral scan and the three-dimensional reconstruction into common locations for registration and combination. At 2408, a three-dimensional model of the anatomy can be created by combining the three-dimensional oral scan with the three-dimensional reconstruction (that are aligned). The view of the three-dimensional model of the anatomy can be altered, partially hidden, rotated, etc. as appropriate for the creation of the custom OSA prevention appliance model (e.g., some of the three-dimensional model of the anatomy can be hidden and/or viewed in two dimensions while the remainder is still visible in three-dimensions).

At 2410, models of two cylinders can be placed within the three-dimensional model of anatomy in an axial plane. The models of the at least two cylinders can guide the design and positioning of each element of the OSA prevention appliance. At 2412, using the cylinders, a model of the OSA prevention appliance for specific anatomy of the patient within the three-dimensional model can be provided. For example, the model of the OSA prevention appliance can be based around the position and orientation of the models of the two cylinders for maximum user tolerance and hold on the collapsing tongue. The OSA prevention appliance and/or parts of the OSA prevention appliance can be manufactured for the patient based on the model. In other words, a hardware device can be made based on the model (created using software and two or more images). This is a common method for produce all OSA prevention appliance, specifically configured based on the specific anatomy of a given user.

Figure 25:
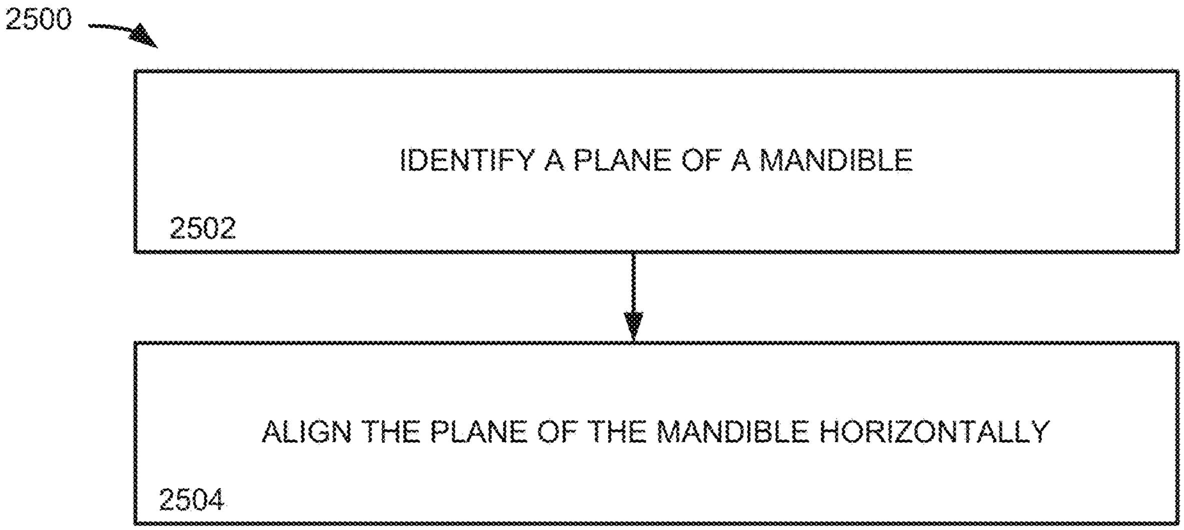

Referring now to FIGS. 25-29, illustrated are methods 2500-2900 for executing an algorithm for producing the custom OSA prevention appliances for a given user's anatomy. FIG. 25 shows a method 2500 for aligning the three-dimensional images. At 2502, the plane of the mandible can be identified. As an example, the plane of the mandible can be identified in the three-dimensional image of the at least the portion of the oral cavity (e.g., the oral scan), but can also be done in the other image (the three-dimensional reconstruction). At 2504, the plane of the mandible can be aligned horizontally. This can be done in either image and/or both images. The three-dimensional reconstruction can be segmented to correct for a tilt of the patient's head in the image. After alignment the two images (e.g., the 3D image and the 3D reconstruction) can be registered together.

Figure 26:
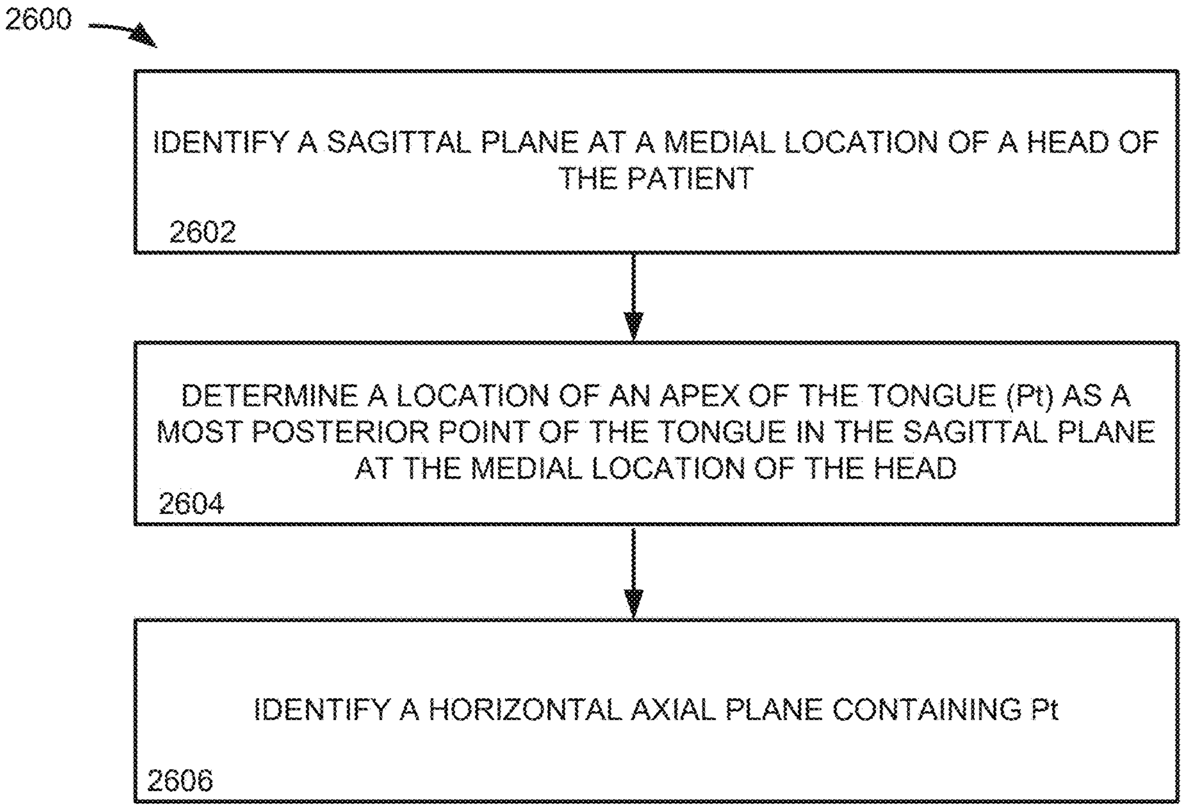

FIG. 26 shows a method 2600 for determining the axial plane on which the entire model of the OSA prevention appliance can be based. At 2602, a sagittal plane can be identified at a medial location of a head of the patient. At 2604, a location on an apex of the tongue (point Pt) can be determined as a most posterior point of the tongue in the sagittal plane at the medial location of the head. At 2606, a horizontal axial plane containing Pt can be identified. Point Pt is an important point for the effective construction (and use) the custom OSA prevention appliance as it acts as a basis for the location and positioned of the wire designed to hold the tongue from collapsing into the oropharynx with best tolerance and swallowing ability. This axial plane can be used (as described in the systems) for the formation of the model of the mouthguard and the models of the cylinders.

Figure 27:
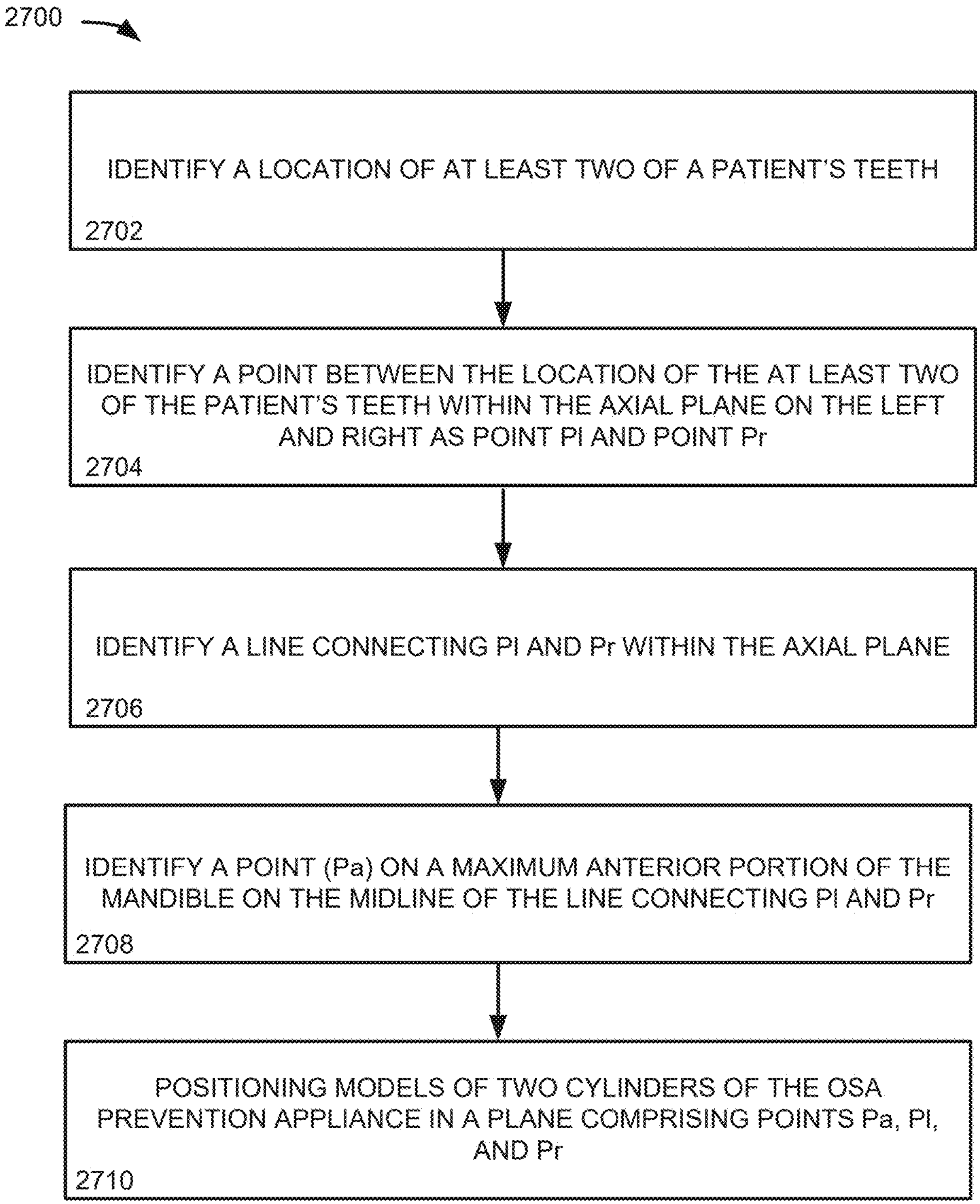

FIG. 27 shows a method 2700 for forming models of two cylinders in the model of the patient's anatomy. Once the models of the cylinders are placed within the model of the anatomy, the OSA prevention appliance (or parts of the OSA prevention apparatus) can be created around the positioning of the model cylinders and the anatomy. At 2702, a location of at least two of a user's teeth can be identified. The patient's teeth can include at least two of a premolar tooth, a first molar tooth, a second molar tooth, and a third molar tooth, on each of a left and right side of the mandible. At 2704, a point between the location of the at least two of the user's teeth can be identified within the axial plane on each of the left and right sides (Pl and Pr). The teeth used to identify the point can depend, for example, on what teeth the user has and/or other constraints. At 2706, a line connecting Pl and Pr can be identified within the axial plane. At 2708, a point (Pa) on a maximum anterior portion of the mandible can be identified and a midline can be drawn connecting point Pa to the line connecting Pl and Pr. At 2710, models are two cylinders of the OSA prevention appliance can be positioned in a plane that includes points Pa, Pl, and Pr. The models of the two cylinders can be oriented in a substantially anterior-posterior direction, can be parallel to each other, and can have a posterior end of each of the models of the two cylinders on the line connecting the point Pl and the point Pr within the axial plane. An anterior end of each of the models of the two cylinders can be located a distance from the mandible.

Figure 28:
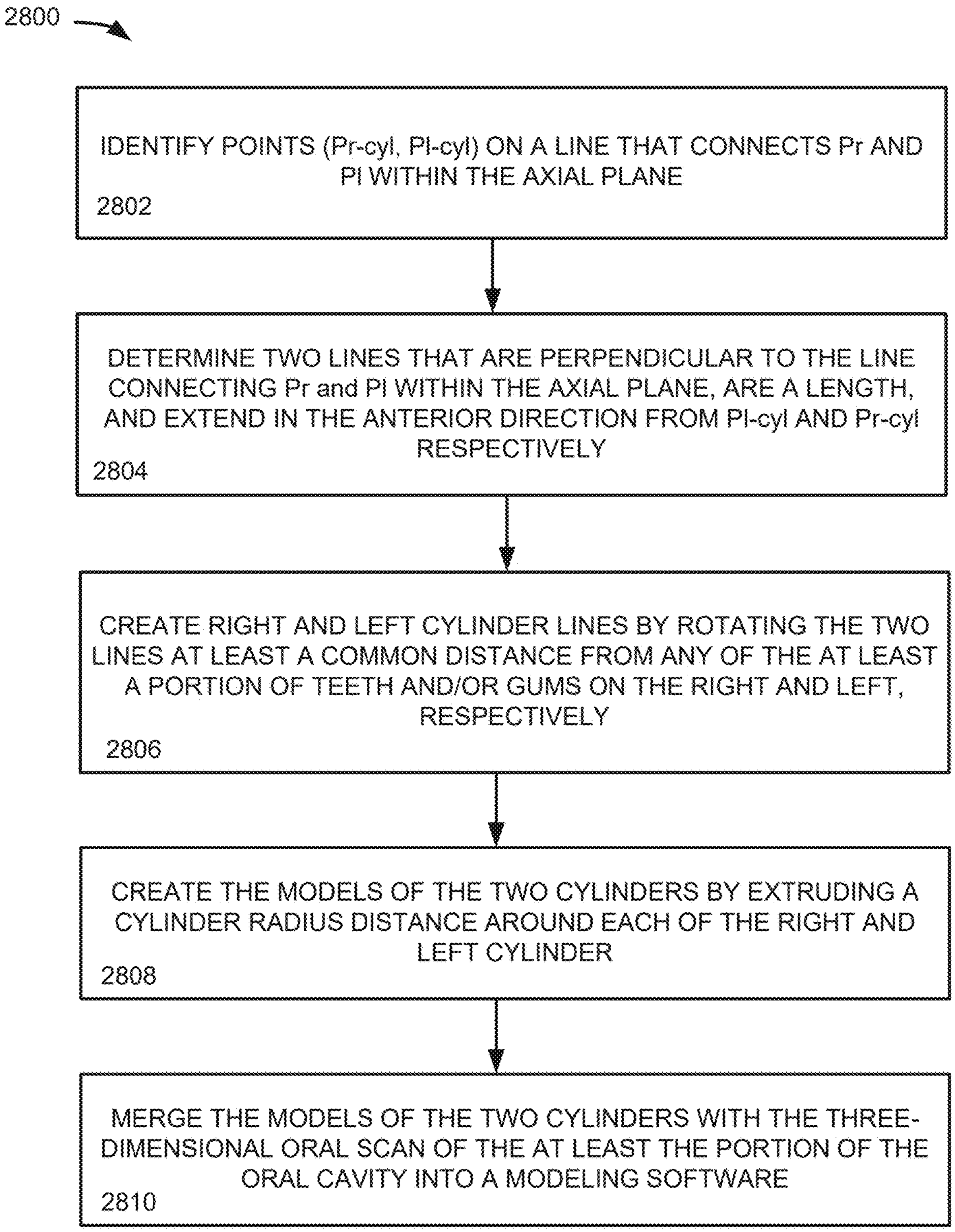

FIG. 28 shows a method 2800 as an alternative method for forming cylinder models and for creating a merged image with the models of the cylinders within the three-dimensional model. At 2802, points Pr-cyl and Pl-cyl can be identified on a line that connects Pr and Pl within the axial plane. Pr-cyl and Pl-cyl can each be a distance from the respective (right and left) lingual side of the teeth/mandible. For example, the distance can be 4 mm. At 2804, two lines that are perpendicular to the line connecting Pr and Pl within the axial plane, are a length, and extend in the anterior direction from Pl-cyl and Pr-cyl, respectively, can be determined. The length can be, for example 18 mm. At 2806, right and left cylinder lines (e.g., the lines on which the model cylinders are based) can be created by rotating the two lines so the lines are at least a common distance from any of the at least a portion of teeth and/or gums on the right and left side, respectively. At 2808, the models of the two cylinders can be created by extruding a cylinder radius distance around each of the right and left cylinder. At 2810, the models of the two cylinders can be merged with the three-dimensional oral scan of at least the portion of the oral cavity into a modelling software (e.g., another portion of the instructions saved in the memory of the modeling system 106).

Figure 29:
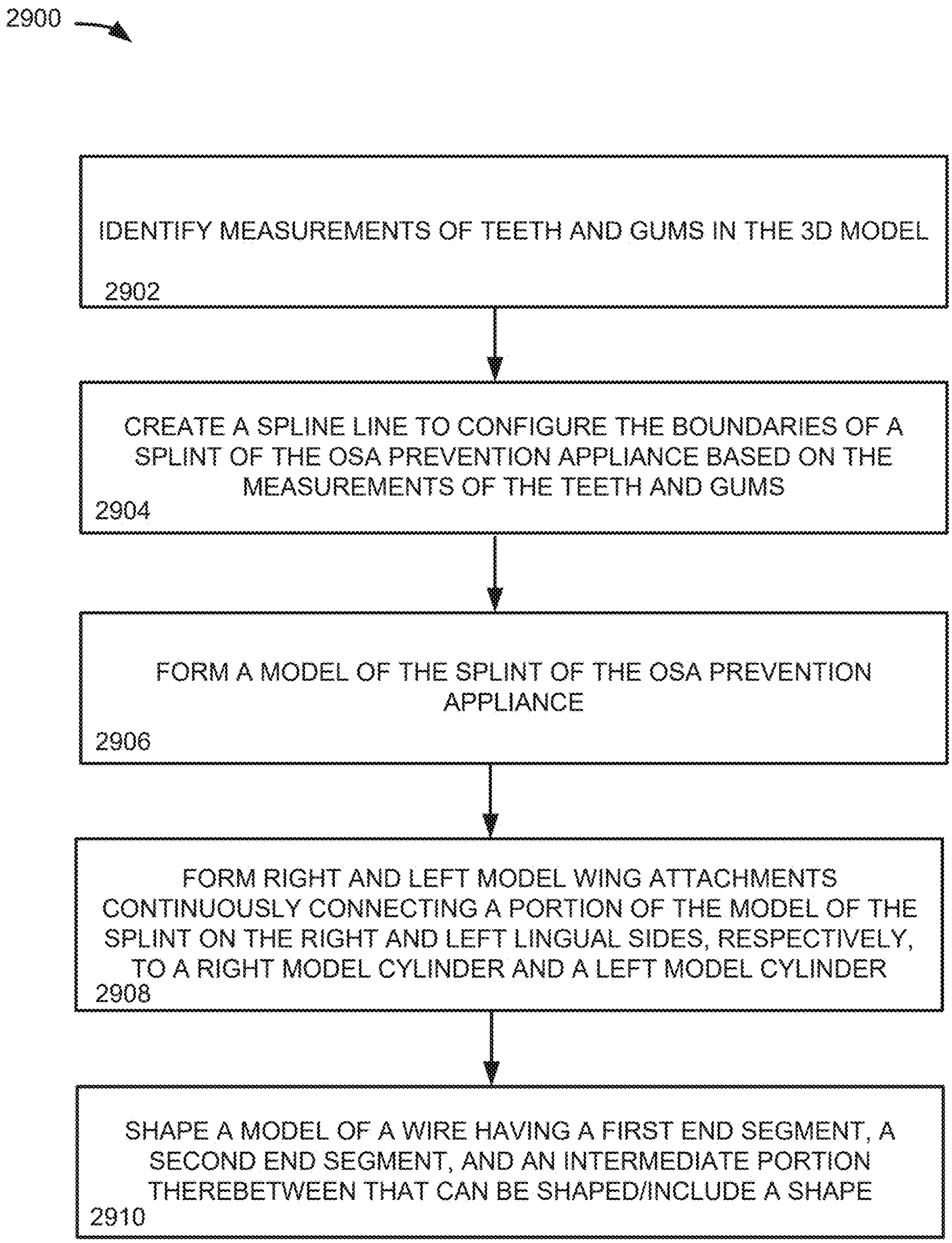

FIG. 29 shows a method 2900 for forming models of the splint (of the mouthguard) and the wire. At 2902, measurements of the teeth and gums can be identified in the three dimensional model of the anatomy. At 2904, a spline line can be created on the gums near the base of the teeth to configure the lower boundaries of a splint of the OSA prevention appliance (e.g., of the mouthguard portion) based on the measurements of the teeth and gums. The upper boundaries can be the top of the teeth and the sides can be the sides of the teeth and gums between the tops of the teeth and the spline line. At 2906, a model of the splint of the OSA prevention appliance can be formed over the teeth and gums. At 2908, right and left model wing attachments can be formed continuously connecting a portion of the model of the splint on the right and left lingual sides to a right model cylinder and a left model cylinder, respectively. At 2910, a model of a wire can be shaped, the wire can have a first end segment, a second end segment, and an intermediate portion therebetween that can be shaped/include a shape. The first end segment starts within one of the models of the two cylinders and the second end segment ends within the other of the models of the two cylinders. The intermediate portion can be shaped to keep a distance from the mandible and to trace along an outline of a posterior surface of at least the tongue. The intermediate portion can be a saddle shape, for example (but it will be understood that the shape is based on the individual's mouth). A separate tongue retention attachment piece can be installed on the saddle shape to better hold the tongue. The tongue retention attachment piece can be modeled by dividing a curved portion of the saddle shape into equal segments equally spaced around the model of the wire and forming a tongue retention attachment model having an annular cross section around the wire of the model. The model tongue retention attachment piece can be split in half and configured to attach around the saddle shape of the model of the wire based on the equal segments when physically formed (e.g., with adhesive, attachment portions, heat, or the like).

Figure 30:
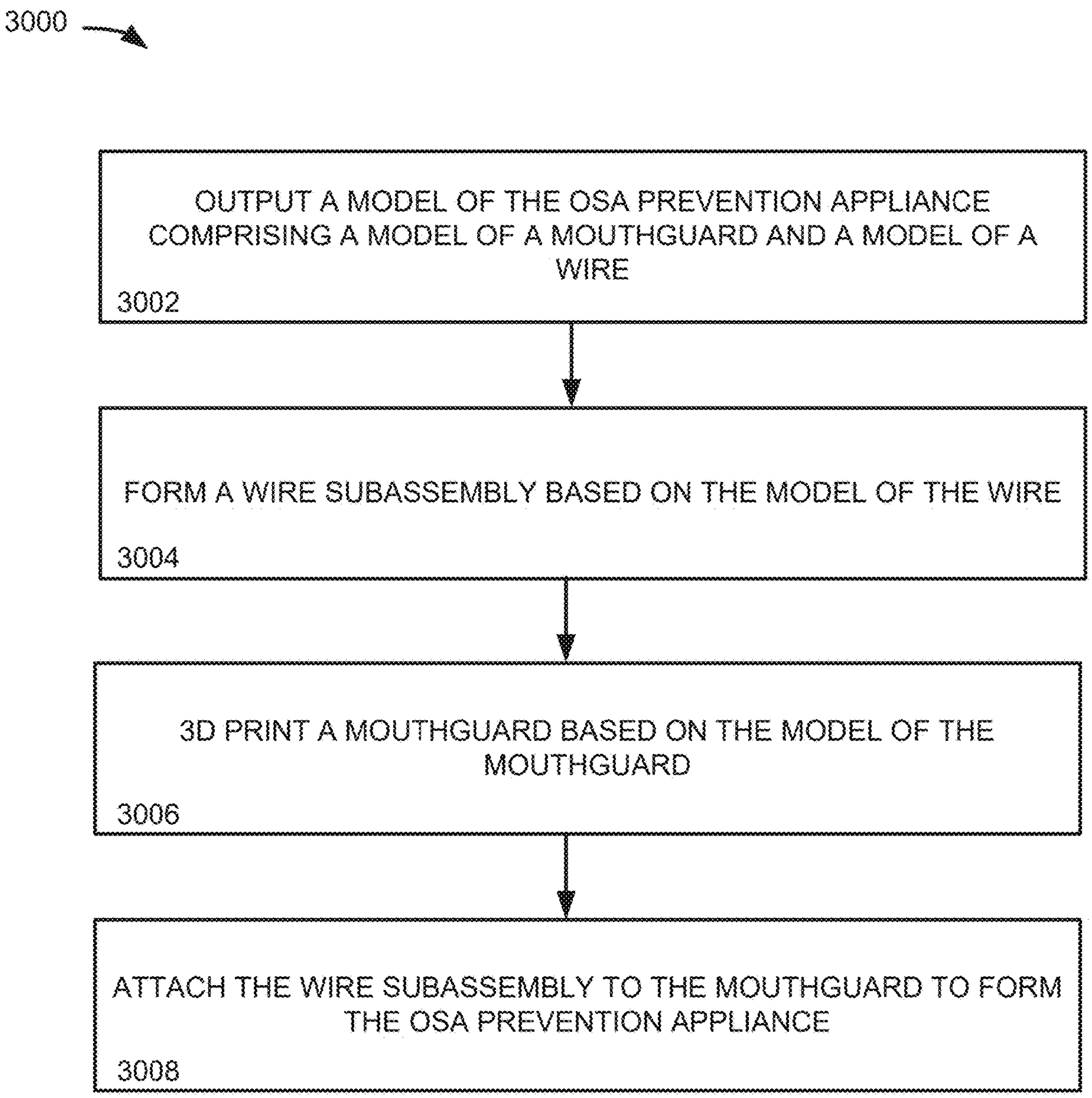

Referring now to FIG. 30, illustrating is a method for producing the hardware custom OSA prevention appliance (in other words, physical manufacture) based on the one or more models. At 3002, a model of the OSA prevention appliance can be output (e.g., to manufacturing system 108). The model can include: at least a model of a mouthguard (the splint plus the left and right wing attachments and the right and left cylinders), a model of a wire, and optionally the tongue retention attachment piece. The left and right cylinders can include interior threading such that wire components can be screwed into the right and left cylinders, respectfully. At 3004, a wire subassembly can be formed based on the model of the wire. The wire sub-assembly can be made, for example, by shaping the intermediate portion of the wire based on the model of the wire and forming a first end segment and a second end segment of the wire based on the model of the wire. Springs can be positioned around a portion of each of the first end segment and the second end segment of the wire and housing components can be positioned over the springs and the wire end segments around at least a portion of the springs and another portion of each of the first end segment and the second end segment of the wire. An exterior of the housing components can be threaded to fit into the threads of the cylinders for attaching the wire subassembly and the mouthguard. Threaded caps can then be fixed to the first and second ends of the wire to hold the springs and the housing components on the first end segment and the second end segment of the wire (optionally washers can also be positioned between the caps and the springs and housings). The first end segment and the second end segment can be connected to the intermediate portion of the wire if the wire comprises multiple parts (such as shown and described with respect to FIG. 22. Of course the wire may be formed in other ways and it will be understood that the intermediate section and the end segments can be contiguous wire, which may have variable size and/or cross-sectional shape. At 3006, a mouthguard can be 3D printed based on the model of the mouthguard. At 3008, a wire sub-assembly (constructed according to the model) can be attached to the mouthguard to form the OSA prevention appliance.

From the above description, those skilled in the art will perceive improvements, changes, and modifications. Such improvements, changes and modifications are within the skill of one in the art and are intended to be covered by the appended claims.

The following is claimed:

1. A method for creating an obstructive sleep apnea (OSA) prevention appliance for a patient, the method comprising:

retrieving, by a system comprising a processor, at least one three-dimensional oral scan comprising at least a portion of an oral cavity of the patient taken with a first imaging modality and a plurality of two-dimensional images of at least another portion of the oral cavity and at least a portion of an oropharynx taken with a second imaging modality different from the first imaging modality, wherein the plurality of two-dimensional images are combined to form a three-dimensional reconstruction of the at least the other portion of the oral cavity and the at least the portion of the oropharynx;

identifying, by the system, at least two anatomical features in the at least one three-dimensional oral scan of the at least the portion of the oral cavity and in the at least one three-dimensional reconstruction of the at least the other portion of the oral cavity and the at least the portion of the oropharynx;

aligning, by the system, the at least two anatomical features in the at least one three-dimensional oral scan of the at least the portion of the oral cavity to the at least two anatomical features in the at least one three-dimensional reconstruction of the at least the other portion of the oral cavity and the at least the portion of the oropharynx;

creating, by the system, a three-dimensional model by combining the at least one three-dimensional oral scan of the at least the portion of the oral cavity within the at least one three-dimensional reconstruction of the at least the other portion of the oral cavity and the at least the portion of the oropharynx;

orienting and placing, by the system, models of two cylinders within the three-dimensional model of anatomy in an axial plane; and providing, by the system, a model of the OSA prevention appliance for specific anatomy of the patient within the three-dimensional model, wherein the model of the OSA prevention appliance is based on the position and orientation of the models of the two cylinders, wherein the OSA prevention appliance is manufactured for the patient based on the model.

2. The method of claim 1, further comprising:

identifying, by the system, a plane of a mandible in the at least one three-dimensional image of the at least the portion of the oral cavity; and aligning, by the system, the plane of the mandible horizontally in the at least one three-dimensional reconstruction of the at least the other portion of the oral cavity and the at least the portion of the oropharynx.

3. The method of claim 2, further comprising segmenting, by the system, the at least one three-dimensional reconstruction of the at least the other portion of the oral cavity and the at least the portion of the oropharynx to correct for a tilt of the patient's head in the image.

4. The method of claim 1, wherein the at least the portion of the oral cavity comprises at least a portion of teeth and/or at least a portion of gums and the at least the other portion of the oral cavity and the at least the portion of the oropharynx comprise: at least a portion of a mandible, at least another portion of the teeth, at least a portion of an interior of the patient's mouth, at least a portion of a tongue, and at least a portion of the oropharynx.

5. The method of claim 4, further comprising:

identifying, by the system, a sagittal plane at a medial location of a head of the patient;

determining, by the system, a location of an apex of the tongue, point Pt, as a most posterior portion of the tongue in the sagittal plane at the medial location of the head; and identifying, by the system, a horizontal axis plane containing the point Pt.

6. The method of claim 5, further comprising:

identifying, by the system, a location of at least two of the patient's teeth, wherein the patient's teeth comprise at least one premolar tooth, a first molar tooth, a second molar tooth, and a third molar tooth, on each of a left and right sides of the mandible; and identifying, by the system, a point between the location of the at least two of the patient's teeth on each of the left and right sides of the mandible within the axial plane as point Pl and point Pr, respectively.

7. The method of claim 6, further comprising:

identifying, by the system, a line connecting the point Pl and the point Pr within the axial plane; and identifying, by the system, a point Pa on a maximally anterior portion of the mandible on the midline of the line connecting the point Pl and the point Pr.

8. The method of claim 7, further comprising positioning, by the system, the models of the two cylinders of the OSA prevention appliance on a plane comprising points Pa, Pl, and Pr such that the models of the two cylinders of the OSA prevention appliance are: oriented in an substantially anterior-posterior direction, parallel to each other, and located on the midline, and a posterior end of each of the models of the two cylinders is on the line connecting the point Pl and the point Pr within the axial plane, and an anterior end of each of the models of the two cylinders is located a distance from the mandible.

9. The method of claim 8, further comprising:

identifying, by the system, a point Pr-cyl and a point Pl-cyl on the line connecting the point Pl and the point Pr within the axial plane, wherein Pr-cyl and Pl-cyl are each a distance from any of the at least the portion of the teeth or the gums on the right and the left, respectively;

determining, by the system, another two lines that are perpendicular to the line connecting the point Pr and the point Pl within the axial plane, are a length, and extend in the anterior direction from the point Pr-cyl and the point Pl-cyl, respectively;

creating, by the system, right and left cylinder center lines, respectively, by rotating the other two lines from each of the point Pr-cyl and the point Pl-cyl until the entire length of the other two lines are at least the distance from any of the at least the portion of the teeth or the gums on the right and the left, respectively; and creating, by the system, the models of the two cylinders by extruding a cylinder radius distance around each of the right and left cylinder center lines; and merging, by the system, the models of the two cylinders with the three-dimensional oral scan of the at least the portion of the oral cavity into a modeling software.

10. The method of claim 8, further comprising:

identifying, by the system, measurements of the teeth and gums of the three-dimensional model;

creating, by the system, a spline line to configure the boundaries of a splint of the OSA prevention appliance based on the measurements of the teeth and gums; and forming, by the system, a model of the splint of the OSA prevention appliance based on the spline line and the measurements of the teeth and gums.

11. The method of claim 10, further comprising:

forming, by the system, right and left model wing attachments continuously connecting a portion of the model of the splint on the right and left lingual sides, respectively, to a right model cylinder and a left model cylinder of the two model cylinders, respectively.

12. The method of claim 11, further comprising shaping, by the system, a model of a wire having a first end segment, a second end segment, and an intermediate portion therebetween, wherein the first end segment of the model of the wire starts within one of the models of the two cylinders and the second end segment of the model of the wire ends within the other of the models of the two cylinders, and wherein the intermediate portion is shaped to keep a distance from the mandible and to trace along an outline of a posterior surface of at least the tongue.

13. The method of claim 12, wherein the intermediate portion of the model of the wire comprises a saddle shape.

14. The method of claim 13, further comprising:

dividing, by the system, a curved portion of the saddle shape into equal segments equally spaced around the model of the wire; and forming, by the system, a tongue retention attachment model having an annular cross section configured to concentrically attach around the saddle shape of the model of the wire based on the equal segments.

15. The method of claim 12, further comprising outputting, by the system the model of the OSA prevention appliance comprising a model of a mouthguard and the model of the wire, wherein the model of the OSA prevention appliance is used for physical manufacture of the OSA prevention appliance, wherein the model of the mouthguard comprises the models of the splint, the right and left wing attachments, and the right and left cylinders.

16. The method of claim 15, further comprising forming a wire subassembly based on the model of the wire by:

shaping an intermediate portion of the wire based on the model of the wire;

forming a first end segment and a second end segment of the wire based on the model of the wire;

positioning springs around a portion of each of the first end segment and the second end segment of the wire;

positioning housing components around at least a portion of the springs and another portion of each of the first end segment and the second end segment of the wire, wherein an exterior of the housing components are threaded;

fixing caps to the first and second ends of the wire, wherein the caps are configured to hold the springs and the housing components on the first end segment and the second end segment of the wire; and connecting the first end segment and the second end segment to the intermediate portion of the wire.

17. The method of claim 16, further comprising three-dimensionally printing a mouthguard based on the model of the mouthguard.

18. The method of claim 17, further comprising forming the OSA prevention appliance by attaching the wire subassembly and the mouthguard together.

19. The method of claim 18, wherein the left and right cylinders comprise interior threading, wherein the right and left ends of the wire subassembly are screwed into the right and left cylinders, respectively.

* * * * *